US011905232B2

(12) United States Patent
Demartis et al.

(10) Patent No.: US 11,905,232 B2
(45) Date of Patent: Feb. 20, 2024

(54) PROCESS OF MAKING 3-(4'-AMINOPHENYL)-2-METHOXYPROPIONIC ACID, AND ANALOGS AND INTERMEDIATES THEREOF

(71) Applicant: Nogra Pharma Limited, Dublin (IE)

(72) Inventors: Salvatore Demartis, Milan (IT); Francesca Viti, Salorino (CH); Marie McNulty, Dublin (IE)

(73) Assignee: Nogra Pharma Limited, Dublin (IE)

( * ) Notice: Subject to any disclaimer, the term of this patent is extended or adjusted under 35 U.S.C. 154(b) by 131 days.

(21) Appl. No.: 17/429,183

(22) PCT Filed: Feb. 10, 2020

(86) PCT No.: PCT/EP2020/053369
§ 371 (c)(1),
(2) Date: Jul. 14, 2022

(87) PCT Pub. No.: WO2020/161362
PCT Pub. Date: Aug. 13, 2020

(65) Prior Publication Data
US 2022/0194894 A1 Jun. 23, 2022

Related U.S. Application Data

(60) Provisional application No. 62/802,802, filed on Feb. 8, 2019.

(51) Int. Cl.
| | | |
|---|---|---|
| *C07C 231/10* | (2006.01) | |
| *C07C 201/12* | (2006.01) | |
| *C07C 205/56* | (2006.01) | |
| *C07C 231/18* | (2006.01) | |
| *C07C 233/54* | (2006.01) | |
| *C07C 231/02* | (2006.01) | |
| *C07C 227/04* | (2006.01) | |
| *C07C 303/28* | (2006.01) | |

(52) U.S. Cl.
CPC .......... *C07C 231/10* (2013.01); *C07C 201/12* (2013.01); *C07C 205/56* (2013.01); *C07C 227/04* (2013.01); *C07C 231/02* (2013.01); *C07C 231/18* (2013.01); *C07C 233/54* (2013.01); *C07C 303/28* (2013.01)

(58) Field of Classification Search
None
See application file for complete search history.

(56) References Cited

U.S. PATENT DOCUMENTS

| | | |
|---|---|---|
| 3,211,610 A | 10/1965 | Rogers |
| 3,444,232 A | 5/1969 | Bernstein |
| 4,036,951 A | 7/1977 | Halpern et al. |
| 4,348,223 A | 9/1982 | Grove |
| 4,404,215 A | 9/1983 | Vincent et al. |
| 4,429,152 A | 1/1984 | Gries et al. |
| 4,720,506 A | 1/1988 | Munakata et al. |
| 4,869,913 A | 9/1989 | Gries et al. |
| 4,933,330 A | 6/1990 | Jorgensen et al. |
| 5,262,549 A | 11/1993 | Telfer et al. |
| 5,302,751 A | 4/1994 | Manimaran et al. |
| 5,519,014 A | 5/1996 | Borody |
| 5,594,015 A | 1/1997 | Kurtz et al. |
| 5,594,151 A | 1/1997 | Stolowitz |
| 6,114,382 A | 9/2000 | Moretti |
| 6,194,627 B1 | 2/2001 | Geissler et al. |
| 6,326,364 B1 | 12/2001 | Lin et al. |
| 6,369,098 B1 | 4/2002 | Pershadsingh et al. |
| 6,403,656 B1 | 6/2002 | Rivier et al. |
| 6,583,128 B2 | 6/2003 | Ekwuribe et al. |
| 6,602,869 B1 | 8/2003 | Galey et al. |
| 6,844,003 B2 | 1/2005 | Galey et al. |
| 6,884,821 B1 | 4/2005 | Shinoda et al. |
| 6,903,082 B2 | 6/2005 | Ekwuribe et al. |
| 7,015,249 B1 | 3/2006 | Vanden Heuvel et al. |
| 7,049,342 B2 | 5/2006 | Miyachi et al. |
| 7,098,025 B1 | 8/2006 | Auwerx et al. |
| 7,176,204 B2 | 2/2007 | Miyachi et al. |
| 7,425,578 B2 | 9/2008 | Ekwuribe et al. |
| 7,429,676 B2 | 9/2008 | Woltering et al. |
| 7,749,980 B2 | 7/2010 | Plourde, Jr. et al. |
| 7,998,474 B2 | 8/2011 | Kelly |
| 8,030,520 B2 | 10/2011 | Sundermeier et al. |
| 8,138,357 B2 | 3/2012 | Naccari et al. |
| 8,153,693 B2 | 4/2012 | Baroni et al. |

(Continued)

FOREIGN PATENT DOCUMENTS

| | | |
|---|---|---|
| CN | 101243039 A | 8/2008 |
| CN | 101878027 A | 11/2010 |

(Continued)

OTHER PUBLICATIONS

Lakshminarayana ("Synthesis and evaluation of some novel isochroman carboxylic acid derivatives as potential anti-diabetic agents" European Journal of Medicinal Chemistry, 44, 2009, p. 3147-3157). (Year: 2009).*
Lee ("Lipase-Catalyzed Transesterification as a Practical Route to Homochiral syn-1,2-Diols. The Synthesis of the Taxol Side Chain" Tetrahedron Lett. 39(1998), p. 2163-2166) (Year: 1998).*
Rao ("Asymmetric Synthesis of Chloramphenicol" J. Chem. Soc., Chem. Commun. 1992, p. 859-860) (Year: 1992).*
Ahnfelt-Ronne et al. (1990) "Clinical Evidence Supporting the Radical Scavenger Mechanism of 5-Aminosalicylic Acid," Gastroenterology, 98(5 Pt 1):1162-9.
Allgayer (2003) "Review Article: Mechanisms of Action of Mesalazine in Preventing Colorectal Carcinoma in Inflammatory Bowel Disease," Aliment Pharmacol Ther, 18(Suppl. 2):10-4.

(Continued)

*Primary Examiner* — Amy C Bonaparte
(74) *Attorney, Agent, or Firm* — Goodwin Procter LLP

(57) ABSTRACT

The disclosure provides a process for the preparation of 3-(4'-aminophenyl)-2-methoxypropionic acid, and analogs and intermediates thereof, contemplated to be capable of modulating the activity of receptors, e.g., PPARs receptors.

19 Claims, No Drawings

(56) References Cited

U.S. PATENT DOCUMENTS

| | | | |
|---|---|---|---|
| 8,153,841 B2 | 4/2012 | Naccari et al. | |
| 8,420,698 B2 | 4/2013 | Lan-Hargest et al. | |
| 8,450,506 B2 | 5/2013 | Naccari et al. | |
| 8,492,438 B2 | 7/2013 | Chung et al. | |
| 8,501,806 B2 | 8/2013 | Baroni et al. | |
| 8,710,100 B2 | 4/2014 | Naccari et al. | |
| 8,754,127 B2 * | 6/2014 | Baroni | A61Q 5/00 514/513 |
| 8,796,282 B2 | 8/2014 | Karnik | |
| 8,796,334 B2 * | 8/2014 | Baroni | A61P 17/10 514/563 |
| 9,133,099 B2 | 9/2015 | Naccari et al. | |
| 9,345,680 B2 | 5/2016 | Naccari et al. | |
| 9,511,041 B2 * | 12/2016 | Baroni | A61Q 5/00 |
| 9,561,202 B2 | 2/2017 | Naccari et al. | |
| 9,682,050 B2 * | 6/2017 | Baroni | A61P 1/12 |
| 9,682,923 B2 | 6/2017 | Baroni et al. | |
| 9,809,557 B2 | 11/2017 | Larsen et al. | |
| 9,901,557 B2 * | 2/2018 | Baroni | A61K 8/42 |
| 9,913,817 B2 | 3/2018 | Baroni et al. | |
| 10,016,381 B2 | 7/2018 | Naccari et al. | |
| 10,137,101 B2 * | 11/2018 | Baroni | C07C 235/38 |
| 10,398,667 B2 * | 9/2019 | Baroni | A61Q 19/06 |
| 10,959,970 B2 * | 3/2021 | Baroni | A61Q 19/06 |
| 11,046,641 B2 | 6/2021 | Baroni et al. | |
| 2003/0113815 A1 | 6/2003 | Houseknecht et al. | |
| 2003/0133875 A1 | 7/2003 | Kelly | |
| 2003/0220374 A1 | 11/2003 | Needleman | |
| 2003/0229083 A1 * | 12/2003 | Debnath | A61P 35/00 514/228.2 |
| 2004/0009956 A1 | 1/2004 | Pei et al. | |
| 2004/0034067 A1 | 2/2004 | MacPhee | |
| 2004/0115127 A1 | 6/2004 | Wright et al. | |
| 2004/0132110 A1 | 7/2004 | Desreumaux et al. | |
| 2005/0277693 A1 | 12/2005 | Palle et al. | |
| 2006/0013775 A1 | 1/2006 | Gristwood et al. | |
| 2006/0159648 A1 | 7/2006 | Davis et al. | |
| 2006/0177444 A1 | 8/2006 | Horizoe | |
| 2006/0270635 A1 | 11/2006 | Wallace et al. | |
| 2007/0065471 A1 | 3/2007 | Jomard et al. | |
| 2007/0086967 A1 | 4/2007 | MacDonald | |
| 2007/0093524 A1 | 4/2007 | Nambi et al. | |
| 2007/0149804 A1 | 6/2007 | Woltering et al. | |
| 2007/0299047 A1 | 12/2007 | Maher et al. | |
| 2009/0042909 A1 | 2/2009 | Karnik | |
| 2009/0048343 A1 * | 2/2009 | Naccari | A61P 35/04 514/567 |
| 2009/0054312 A1 | 2/2009 | Wolf et al. | |
| 2009/0118357 A1 * | 5/2009 | Naccari | C07C 229/64 549/470 |
| 2010/0041617 A1 | 2/2010 | Trepel et al. | |
| 2010/0305077 A1 | 12/2010 | Baroni et al. | |
| 2011/0105748 A1 | 5/2011 | Bhuniya et al. | |
| 2011/0152225 A1 | 6/2011 | Baroni et al. | |
| 2011/0288058 A1 | 11/2011 | Baroni et al. | |
| 2011/0288177 A1 | 11/2011 | Baroni et al. | |
| 2012/0053244 A1 * | 3/2012 | Baroni | A61Q 5/00 562/455 |
| 2012/0053245 A1 | 3/2012 | Baroni et al. | |
| 2012/0100223 A1 | 4/2012 | Bhagat | |
| 2012/0157417 A1 | 6/2012 | Baroni et al. | |
| 2012/0195980 A1 | 8/2012 | Shaver | |
| 2012/0316230 A1 | 12/2012 | Naccari et al. | |
| 2013/0005813 A1 | 1/2013 | Naccari et al. | |
| 2015/0045436 A1 | 2/2015 | Naccari et al. | |
| 2015/0051285 A1 | 2/2015 | Baroni et al. | |
| 2015/0087678 A1 | 3/2015 | Baroni et al. | |
| 2015/0087708 A1 | 3/2015 | Baroni et al. | |
| 2015/0148418 A1 | 5/2015 | Baroni et al. | |
| 2015/0250749 A1 * | 9/2015 | Giuliani | A61P 17/14 514/567 |
| 2015/0265514 A1 | 9/2015 | Giuliani et al. | |
| 2015/0265562 A1 | 9/2015 | Naccari et al. | |
| 2015/0265563 A1 | 9/2015 | Naccari et al. | |
| 2016/0160867 A1 | 6/2016 | Gehlot | |
| 2016/0338927 A1 | 11/2016 | Baroni et al. | |
| 2017/0056349 A1 | 3/2017 | Baroni et al. | |
| 2017/0172956 A1 | 6/2017 | Baroni et al. | |
| 2017/0312239 A1 | 11/2017 | Naccari et al. | |
| 2018/0064667 A1 | 3/2018 | Baroni et al. | |
| 2018/0065921 A1 | 3/2018 | Baroni et al. | |
| 2018/0099920 A1 | 4/2018 | Holm Pedersen et al. | |
| 2018/0193361 A1 | 7/2018 | Winer et al. | |
| 2018/0222880 A1 | 8/2018 | Wang et al. | |
| 2018/0369178 A1 | 12/2018 | Baroni et al. | |
| 2019/0046490 A1 | 2/2019 | McNulty et al. | |
| 2019/0269637 A1 | 9/2019 | Baroni et al. | |
| 2020/0188340 A1 | 6/2020 | Baroni et al. | |
| 2020/0383942 A1 | 12/2020 | Baroni et al. | |
| 2021/0113505 A1 | 4/2021 | Giuliani et al. | |
| 2022/0000818 A1 | 1/2022 | Bellinvia et al. | |
| 2022/0033346 A1 | 2/2022 | Baroni et al. | |

FOREIGN PATENT DOCUMENTS

| | | |
|---|---|---|
| CN | 105566153 A | 5/2016 |
| EP | 0055689 A1 | 7/1982 |
| EP | 0102833 A1 | 3/1984 |
| EP | 0115419 A2 | 8/1984 |
| EP | 0279096 A2 | 8/1988 |
| EP | 0291159 A2 | 11/1988 |
| EP | 0352826 A2 | 1/1990 |
| EP | 0623104 B1 | 8/1997 |
| EP | 0938459 B1 | 7/2002 |
| EP | 1285908 A1 | 2/2003 |
| EP | 1348698 A1 | 10/2003 |
| EP | 0554291 B1 | 12/2003 |
| EP | 1373906 A1 | 1/2004 |
| EP | 1389044 A1 | 2/2004 |
| EP | 1607103 A1 | 12/2005 |
| EP | 1274407 B1 | 3/2006 |
| EP | 1719543 A1 | 11/2006 |
| EP | 1801093 B1 | 3/2009 |
| EP | 1448995 B1 | 1/2011 |
| EP | 2298321 A1 | 3/2011 |
| EP | 2107047 B1 | 9/2011 |
| EP | 2926807 A1 | 10/2015 |
| GB | 767788 A | 2/1957 |
| GB | 1359560 | 7/1974 |
| JP | 2003-516310 A | 5/2003 |
| JP | 3425441 B2 | 7/2003 |
| JP | 3435651 B2 | 8/2003 |
| JP | 2004-528329 A | 9/2004 |
| JP | 2005-510733 A | 4/2005 |
| JP | 2009-242399 A | 10/2009 |
| JP | 2010-520166 A | 6/2010 |
| JP | 2015-506193 A | 3/2015 |
| JP | 2015-518483 A | 7/2015 |
| WO | WO-1992/006690 A1 | 4/1992 |
| WO | WO-1993/014056 A1 | 7/1993 |
| WO | WO-93/19053 A1 | 9/1993 |
| WO | WO-1994/000135 A1 | 1/1994 |
| WO | WO-1995/031194 A1 | 11/1995 |
| WO | WO-1996/030016 A2 | 10/1996 |
| WO | WO-1997/025042 A1 | 7/1997 |
| WO | WO-1998/006387 A2 | 2/1998 |
| WO | WO-1998/043081 A1 | 10/1998 |
| WO | WO-1999/015520 A1 | 4/1999 |
| WO | WO-1999/29317 A1 | 6/1999 |
| WO | WO-2000/059866 A1 | 10/2000 |
| WO | WO-2000/062766 A2 | 10/2000 |
| WO | WO-2001/002388 A1 | 1/2001 |
| WO | WO-2001/025181 A1 | 4/2001 |
| WO | WO-2001/066067 A1 | 9/2001 |
| WO | WO-2001/079153 A1 | 10/2001 |
| WO | WO-2002/046161 A1 | 6/2002 |
| WO | WO-2002/077651 A1 | 10/2002 |
| WO | WO-2002/085123 A1 | 10/2002 |
| WO | WO-2002/095393 A2 | 11/2002 |
| WO | WO-2003/033456 A1 | 4/2003 |
| WO | WO-2003/033481 A1 | 4/2003 |
| WO | WO-2003/043569 A2 | 5/2003 |
| WO | WO-2003/046580 A1 | 6/2003 |

(56) References Cited

FOREIGN PATENT DOCUMENTS

| WO | WO-2003/048116 A2 | 6/2003 |
|---|---|---|
| WO | WO-2003/053974 A1 | 7/2003 |
| WO | WO-2004/037810 A1 | 5/2004 |
| WO | WO-2004/073622 A2 | 9/2004 |
| WO | WO-2005/012280 A1 | 2/2005 |
| WO | WO-2005/040102 A2 | 5/2005 |
| WO | WO-2005/072113 A2 | 8/2005 |
| WO | WO-2005/084658 A1 | 9/2005 |
| WO | WO-2006/072175 A1 | 7/2006 |
| WO | WO-2007/010514 A2 | 1/2007 |
| WO | WO-2007/010516 A2 | 1/2007 |
| WO | WO-2007/096148 A1 | 8/2007 |
| WO | WO-2008/094618 A2 | 8/2008 |
| WO | WO-2008/104557 A1 | 9/2008 |
| WO | WO-2009/025854 A1 | 2/2009 |
| WO | WO-2009/080828 A2 | 7/2009 |
| WO | WO-2009/135911 A1 | 11/2009 |
| WO | WO-2010/063470 A2 | 6/2010 |
| WO | WO-2010/063472 A1 | 6/2010 |
| WO | WO-2010/091892 A2 | 8/2010 |
| WO | WO-2010/091894 A2 | 8/2010 |
| WO | WO-2013/012662 A2 | 1/2013 |
| WO | WO-2013/059364 A2 | 4/2013 |
| WO | WO-2013/064153 A1 | 5/2013 |
| WO | WO-2013/117744 A9 | 8/2013 |
| WO | WO-2013/156413 A1 | 10/2013 |
| WO | WO-2013/168438 A1 | 11/2013 |
| WO | WO-2013/178815 A1 | 12/2013 |
| WO | WO-2013/178816 A1 | 12/2013 |
| WO | WO-2014/041140 A1 | 3/2014 |
| WO | WO-2014/041141 A1 | 3/2014 |
| WO | WO-2014/154683 A1 | 10/2014 |
| WO | WO-2016/154730 A1 | 10/2016 |
| WO | WO-2016/202341 A1 | 12/2016 |
| WO | WO-2017/046343 A1 | 3/2017 |
| WO | WO-2017/093444 A1 | 6/2017 |
| WO | WO-2017/144725 A1 | 8/2017 |
| WO | WO-2020/152350 A1 | 7/2020 |
| WO | WO-2020/161362 A1 | 8/2020 |

OTHER PUBLICATIONS

Ameho et al., (1997) 'Prophylactic Effect of Dietary Glutamine Supplementation on Interleukin 8 and Tumor Necrosis Factor Alpha Production in Trinitrobenzene Sulphonic Acid Induced Colitis,' Gut, 41(4):487-93.
Australian Examination Report dated Jan. 31, 2014, for Application No. 2009321722 (9 pages).
Azhar, (2010), 'Peroxisome Proliferator-Activated Receptors, Metabolic Syndrome and Cardiovascular Disease,' Future Cardiol, 6(5):657-91 (NIH Public Access Author Manuscript).
Baker et al., (1962) "Potential Anticancer Agents. LXXVIII Nonclassical Antimetabolites. IV. Synthesis of Compounds Related to 4-(Iodoacetamido) Salicylic Acid, an Exo-Alkylating Irreversible Inhibitor," J Org Chem, 27(9):3283-95.
Bassaganya-Riera J et al., (2011), 'Activation of PPARγ and σ by Dietary Punicic Acid Ameliorates Intestinal Inflammation in Mice,' Br J Nutr, 106(6):878-86.
Bassaganya-Riera, et al."Activation of PPAR γ and σ by conjugated linoleic acid mediates protection from experimental inflammatory bowel disease," Gastroenterology, 127(3): 777-791, (2004).
Baz et al. (2003) 'Oxidant / Antioxidant Status in Patients with Psoriasis,' Yonsei Med J, 44(6):987-90.
Behshad et al., (2008) 'A Retrospective Case Series Review of the Peroxisome Proliferator-Activated Receptor Ligand Rosiglitazone in the Treatment of Atopic Dermatitis,' Arch Dermatol, 144(1):84-8.
Beilstein Database Beistein Institute zur Forderung der Chemischen Wissenschaften, Frankfurt an Main, DE XP002413839, Accession No. 2092096, J. Med. Chem., 22: 589 (1979).
Beilstein Database, Beilstein Institute for Organic Chemistry, Frankfurt an Main, DE, retrieved from XFIRE, Accession No. brn 2208094, J. Am. Chem. Soc., 68: 2335, 2338 (1946).
Beilstein Database, Beilstein Institute for Organic Chemistry, Frankfurt an Main, DE, retrieved from XFIRE, Accession No. brn 2803076, J. Org. Chem., 14: 1013, 1018 (1949).
Beilstein Database, Beilstein Institute for Organic Chemistry, Frankfurt an Main, DE, retrieved from XFIRE, Accession No. brn 3199913, Chem. Ber., 46: 3978 (1913).
Beilstein Database, Beilstein Institute for Organic Chemistry, Frankfurt an Main, DE, retrieved from XFIRE, Accession No. brn 3200601, J. Chem. Soc., pp. 104, 111 (1935).
Beilstein Database, Beilstein Institute for Organic Chemistry, Frankfurt an Main, DE, retrieved from XFIRE, Accession No. brn 3268495, Justus Liebigs Ann. Chem., 463:60 (1924).
Beilstein Database, Beilstein Institute for Organic Chemistry, Frankfurt an Main, DE, retrieved from XFIRE, Accession No. brn 3296969, Chem. News J. Ind. Sci, 36: 269 (1877).
Beilstein Database, Beilstein Institute for Organic Chemistry, Frankfurt an Main, DE, retrieved from XFIRE, Accession No. pcrn 859019, U.S. Pat. No. 4,429,152 A (Jan. 1984).
Beilstein Database, Beilstein Institute for Organic Chemistsry, Frankfurt an Main, DE, retrieved from XFIRE, Accession No. brn 3199917, Chem. Ber., 46: 288 (1913).
Beilstein Database, Beilstsein Institute for Organic Chemistry, Frankfurt an Main, DE, retrieved from XFIRE, Accession No. brn 3242057, Chem. Ber., 74: 500, 517 (1941).
Beilstein Database, Beistein Institut zur Forderung der Chemischen Wissenschaften, Frankfurt an Main, DE, XP002413837, Accession No. 2367395, Chem. Ber., 87: 179-181 (1954.).
Beilstein Database, Beistein Institut zur Forderung der Chemischen Wissenschaften, Frankfurt an Main, DE, XP002413838, Accession No. 2839685, J. Am. Chem Soc., 73: 903-904 (1951).
Beilstein Database, Beistein Institut zur Forderung der Chemischen Wissenschaften, Frankfurt an Main, DE, XP002413840, Accession No. 3031462, Bull Soc. Chim Belg., 61: 310-320 (1952).
Beilstein Database, Beistein Institut zur Forderung der Chemischen Wissenschaften, Frankfurt an Main, DE, XP002413842, Accession No. 3259704, Justus Liebigs Ann Chem, 429: 173 (1922).
Beilstein Database, Beistein Institut zur Förderrung der Chemischen Wisssenschaften, Frankfurt an Main, DE, XP002413836, Accession No. 1869425, J. Labelled Compd Radiopharm, 44: S225-S227 (2001).
Beilstein Database, Beisten Insstitut zur Forderung der Chemischen Wissenschaften, Frankfurt an Main, DE, XP002413843, Accession No. 3530419, Justus Liebigs Ann Chem, 429: 164 (1922).
Beilstein Database, Beisten Institut zur Forderung der Chemischen Wissenschaften, Frankfurt an Main, DE, XP002413841, Accession No. 2641495, J. Org. Chem., 27: 3283-3295 (1962).
Bickers et al., (2006) 'Oxidative Stress in the Pathogenesis of Skin Disease,' J Invest Dermatol, 126(2):2565-75.
Bongartz et al., (2005) 'Treatment of Active Psoriatic Arthritis with the PPARγ Ligand Pioglitazone: An Open-Label Pilot Study,' Rheumatology, 44(1):126-9.
Broadwith (2009) "Enzyme Binds Both Sides of the Mirror," Chem World, Nov. 6, 2009, https://www.chemistryworld.com/news/enzyme-binds-both-sides-of-the-mirror/1016647.article (2 pages).
Brown and Joyeau, (1979), 'Use of p-Aminophenyl D and L-Lactic Acids and p-Aminophenyl Pyruvic Acid as Effectors in the Affinity Chromatography of Lactate Dehydrogenase,' Biochimie, 61(3):437-42 (Abstract only).
Brown et al., (1978) "Chimie Organique," C.R. Acad. Sc. Paris, t. 287:125-8.
Brunton et al., (1997) "A Role of Epidermal Growth Factor Receptor, c-Src and Focal Adhesion Kinase in an in vitro Model for the Progression of Colon Cancer," Oncogene, 14( 3):283-93.
Bull (2003) "The Role of Peroxisome Proliferator-Activated Receptor γ in Colon Cancer and Inflammatory Bowel Disease," Arch Pathol Lab Med, 127(9):1121-3.
CAPLUS file accession No. 2007:857379, document No. 148:517389, Indian patent No. IN2003CH01004, published on Jul. 27, 2007.
Casen Recordati Group, (2016), 'Cleen Ready-to-Use Enema, Summary of Product Characteristics Updated Jun. 16, 2016,' emc+, medicines.org. UK/emc, XP-002763390, <https://www.medicines.org.UK/emc/print-document?documentId=542>, [retrieved Oct. 25, 2016] (5 pages).

(56) References Cited

OTHER PUBLICATIONS

Casen Recordati Group, (2016), 'Cleen Ready-to-Use Enema,' emc+, medicines.org. UK/emc, XP-002763391, <https://www.medicines.org.UK/emc/history/542#version9>, [retrieved Oct. 25, 2016] (2 pages).
Clark et al., (1989) "Validation of the General Purpose Tripos 5.2 Field," J. Comput Chem, 10(8):982-1012.
Collino et al., (2006) "Modulation of the Oxidative Stress and Inflammatory Response by PPAR-gamma Agonists in the Hippocampus of Rats Exposed to Cerebral Ischemia/Reperfusion," Eur J Pharmacol, 530(1-2):70-80.
Corse et al., (1948) "Biosythesis of Penicillins" J Am Chem Soc, 70(9):2837-43.
Database CA [Online] Chemical Abstracts Service, Columbus Ohio, US; Database Accession No. 67:50608, Abstract of Baker et al.: "Irreversible Enzyme Inhibitors. LXXXVII. Hydrophobic Bonding to dihydrofolic reductase. 9. Mode of Binding of m-aryloxyalkyl groups on, 6-diamino-1,2-dihydro-2,2-dimethyl-1-phenyl-s-triazine", (1967).
Database CA [Online] Chemical Abstracts Service, Columbus, Ohio, US, Database Accession No. 107:235800, Abstract of Cleary, et al., "Methylenecyclopropane rearrangement as a probe for free radical substituent effects. . sigma. . bul. Values for commonly encountered conjugating and organometallic groups", (1987).
Database CA [Online] Chemical Abstracts Service, Columbus, Ohio, US, Database Accession No. 111:153586, Abstract of Gonzalez, et al., ".alpha.- Amino carbanions. A second generation formamidine for facile deprotonation leading to .alpha.-quaternary substitution", (1989).
Database CA [Online] Chemical Abstracts Service, Columbus, Ohio, US, Database Accession No. 119:95018, Abstract of Yoon, et al., "Reduction of nitro compounds with borohydride exchange resin-nickel acetate", (1993).
Database CA [Online] Chemical Abstracts Service, Columbus, Ohio, US, Database Accession No. 131:144358, Abstract of Lamy-Pitara, et al., "Selective Catalytic Hydrogenation of Unsaturated Derivatives of Nitrobenzene in Alcoholic Media", (1999).
Database CA [Online] Chemical Abstracts Service, Columbus, Ohio, US, Database Accession No. 50:52519, Abstract of Pratt, et al., "Reaction rates by distillation. VI. The etherification of benzyl and related alcohols", (1956).
Database CA [Online] Chemical Abstracts Service, Columbus, Ohio, US, Database Accession No. 8:526, Abstract of Schepss, "Electrolytic reduction of aldehydes", (1914).
Database CA [Online] Chemical Abstracts Service, Columbus, Ohio, US, Database Accession No. 2010:351508, Abstract of Baroni, et al., "Compounds for the selective treatment of intestinal immuninflammatory component of the celiac disease", (2007).
Database CA [Online] Chemical Abstracts Service, Columbus, Ohio, US, Database Document No. 118:101608, Accession No. 1993:101608, Abstract of Breuer, et al., "An efficient synthesis of ethyl 3'-aminocinnamate", (1992).
Database CA [Online] Chemical Abstracts Service, Columbus, Ohio, US: Database Accession No. 96:19761, Abstract of Macek et al., "Studies on Local Anesthetics LXXIV. Basic esters of o-(m-)(alkoxymethyl)carbanilic acids", (1981).
Database CA [Online] Chemical Abstracts Service, Columbus, Ohio, US; Database Accession No. 105:24135, Abstract of Wulff, et al., "Chemistry of binding sites. VI. On the suitability of various aldehydes and ketones as binding sites for monoalcohols", (1986).
Database CA [Online] Chemical Abstracts Service, Columbus, Ohio, US; Database Accession No. 110:194186, Abstract of Pei et al., "A Lewis acid catalyst supported by polymers-styrene-methyl methacrylate copolymer-titanium tetrachloride complex preparation and uses in organic synthesis", (1989).
Database CA [Online] Chemical Abstracts Service, Columbus, Ohio, US; Database Accession No. 112:157479, Abstract of Joshi et al., "Catalysis by heteropoly acids: some new aspects", (1989).
Database CA [Online] Chemical Abstracts Service, Columbus, Ohio, US; Database Accession No. 121:204747, Abstract of Yang et al., "Photosolvolysis of 2-aminobenzyl alcohol in aqueous solution", (1994).
Database CA [Online] Chemical Abstracts Service, Columbus, Ohio, US; Database Accession No. 131:228419, Abstract of Engell et al., "The Decomposition of methyl hemiacetals of benzaldehyde in aqueous solution: a study of the effect of aromatic substitution", (1999).
Database CA [Online] Chemical Abstracts Service, Columbus, Ohio, US; Database Accession No. 135:180359, Abstract of Pitts et al., "Indium metal as a reducing agent in organic synthesis", (2001).
Database CA [Online] Chemical Abstracts Service, Columbus, Ohio, US; Database Accession No. 49:68907, Abstract of Mann, et al., "The action of magnesium and of Grignard reagents on certain benzyl ethers. II. The action of Grignard reagents on .omicron.-, m-, and p-(methoxy- and phenoxymethyl) anilines", (1954).
Database CA [Online] Chemical Abstracts Service, Columbus, Ohio, US; Database Accession No. 66:37529, Abstract of Minisci, et al., "Orientation in the radical amination of aromatic compounds with N-chlorodimethylamine-competition between nuclear and benzylic attack", (1966).
Database CA [Online] Chemical Abstracts Service, Columbus, Ohio, US; Database Accession No. 84:4573, Abstract of Gale, et al., "Amidomethylation of some N,N-dialkylanilines (Tscherniac-Einhorn reaction)", (1975).
Database CA Registry [Online] Chemical Abstracts Service, Columbus, Ohio, US; Database Accession No. 1001756-73-5, Abstract & "Allichem Catalog" Jun. 3, 2009; XP002595814, (2008).
Database Caplus Chemical Abstracts Service, Columbus, Ohio, US; Database Accession No. 1913:10241, Abstract of Heller: Berichte der Deutschen Chemischen Gesellschaft (1913), 46:280-294.
Database Caplus Chemical Abstracts Service, Columbus, Ohio, US; Database Accession No. 1949:23214, Abstract of Tomcsik et al.: Helvetica Chimica Acta (1949), 32:31-34.
Database Caplus Chemical Abstracts Service, Columbus, Ohio, US; Database Accession No. 1955:19868, Abstract of Mann et al.: Chemistry & Industry (London, United Kingdom) (1954) 373-374.
Database Caplus Chemical Abstracts Service, Columbus, Ohio, US; Database Accession No. 1979:18291, Abstract of Brown et al.: "Affinity Chromatography of L-lactate dehydrogenase (LDH) on Synthetic Supports. Preparation and Immobilization of D- and L-p-aminophenyllactic Acids, New Effectors of LDH." Comptes Rendus des Seances de l'Academic des Scie. 287(4):125-128 (1978).
Database Caplus Chemical Abstracts Service, Columbus, Ohio; Database Accession No. 1925:25469, Abstract of Sherwin: "Acetylation as a Physiologic Reaction." Proceedings of the Society for Experimental Biology and Medicine (1924), 22:182.
Database Caplus Chemical Abstracts Service, Columbus, Ohio; Database Accession No. 1967:490291, Abstract of Deljac et al.: "Absolute Configuration of (--)-β-hydroxy-β-(m-hydroxyphenyl) propionic acid", Recueill des Travaux Chimiques des Pays-Bas (1967), 68(8):765-768.
Database Chemcats [Online] Chemical Abstracts Service, Columbus, Ohio, US; Accession No. 2058162244, Allichem Product List, Jun. 3, 2009; XP002591674, Feb. 6, 2008.
Delbarre et al., (1964), Chemical Abstracts, vol. 65, Columbus , Ohio, Abstract No. 93711, "Non-steroid Antiinflammatory Substances. I. Derivatives of the 4- and 5- Aminosalicylic Acids," Med Exp Int J Exp Med, 11:389-96.
Deljac et al., (1967) "Absolute Configuration of (-)-β-Hydroxy-β-(m)-Hydroxyphenyl)-Propionic Acid," Recueil des Travaux Chimiques des Pays-Bas, 86:765-8.
Di Gregorio, J. et al. "Role of glycogen synthase kinase-3? and PPAR-? on epithelial-to-mesenchymal transition in DSS-induced colorectal fibrosis," PLoS One (2017), 12(2), e0171093/1-e0171093/23.
Dimon-Gadal et al., (2000) 'Increased Oxidative Damage to Fibroblasts in Skin With and Without Lesions in Psoriasis,' J Invest Dermatol, 114(5):984-9.
Ding, et al., (2012) "Mucosal Healing and Fibrosis after Acute or Chronic Inflammation in Wild Type FVB-N Mice and C57BL6

(56) References Cited

OTHER PUBLICATIONS

Procollagen α1 (I)-Promoter-GFP Reporter Mice", PLoS ONE, vol. 7, No. 8, p. e42568, XP055433727.
DiPoï et al., (2004) 'Functions of Peroxisome Proliferator-Activated Receptors (PPAR) in Skin Homeostasis,' Lipids, 39(11):1093-9.
DiPoï et al., (2005) 'Epithelium-Mesenchyme Interactions Control the Activity of Peroxisome Proliferator-Activated Receptor β/δ During Hair Follicle Development,' Mol Cell Biol, 25(5):1696-1712 (2005).
Doshi et al., (1997) "A Comparison of Current Acne Grading Systems and Proposal of a Novel System," Int J Dermatol, 36(6):416-8.
Drosner M et al., (2005), 'Photo-Epilation: Guidelines for Care from the European Society for Laser Dermatology (ESLD),' J Cosmet Laser Ther, 7(1):33-8.
Dubuquoy et al., (2002) "Role of peroxisome proliferator-activated receptor γ and retinoid X receptor heterodimer in hepatogastroenterological diseases," Lancet, 360(9343):1410-8.
Dubuquoy et al., (2003) "Impaired Expression of Peroxisome Proliferator-Activated Receptor Gamma in Ulcerative Colitis," Gastroenterology, 124(5):1265-76.
Dyall-Smith, D, "Lichen Planopilaris," , 2011, pp. 1-4 [online] [retrieved on Mar. 29, 2018] Retrieved from http://www.dermnetnz.org/topics/lichen-planopilaris.
Egan et al., (2003) "Clinical Pharmacology in Inflammatory Bowel Disease: Optimizing Current Medical Therapy," *Inflammatory Bowel Disease: From Bench to Bedside*, (2$^{nd}$ Ed, 2003), Stephan R Targan et al. (Eds), Springer Publishingm New York, NY (Publ), pp. 495-521.
Ellis et al., (2007) "Placebo Response in Two Long-Term Randomized Psoriasis Studies that were Negative for Rosiglitazone," Am J Clin Dematol, 8(2):93-102.
European Clinical Trials Register, (2012), entry EudraCT No. 2011-003283-78 [online] Mar. 1, 2012, [retrieved from the internet at <https://www.clinicaltrialsregister.eu/ctr-search/trial/2011-003283-78/IT> on Feb. 1, 2017] European Union Clinical Trials Register, XO-002766683 (6 pages).
Examination Report dated Apr. 15, 2011 for Application No. 06 766 083.7-2103 (11 pages).
Fernholz et al., (1992) "Specificity of Antibody-Catalyzed Transesterifications Using Enol Esters: A Comparison with Lipase Reactions," J Org Chem, 57(17):4756-61.
Floch and White, (2006), 'Management of Diverticular Disease is Changing,' World J Gastroenterol, 12(20):3225-8.
Fu Xiaoxia et al. (2010) "Advance on PPARγ and ligands thereof and liver fibrosis," Chinese Journal of Clinical Gastroenterology 22(4):254-256.
Fuenzalida et al., (2007) "Peroxisome Proliferator-activated Receptor Gamma Up-regulates the Bcl-2 Anti-apoptotic Protein in Neurons and Induces Mitochondrial Stabilization and Proection against Oxidative Stress and Apoptosis," J Biol Chem, 282(51):37006-15.
Gampe et al., (2000) "Asymmetry in the PPARγ/RXRα Crystal Structure Reveals the Molecular Basis of Heterodimerization Among Nuclear Receptors," Mol Cell, 5(3):545-55.
Garza LA et al., (2011), 'Bald Scalp in Men with Androgenetic Alopecia Retains Hair Follicle Stem Cells but Lacks CD200-Rich and CD34-Positive Hair Follicle Progenitor Cells,' J Clin Invest, 121(2):613-22.
Gerdes et al., (1986) "Growth Fractions in Breast Cancers Determined in Situ with Monoclonal Antibody Ki-67," J Clin Pathol, 39(9):977-80.
GlaxoSmithKline. (2008) Scientific Result Summary for Clinical Study ID 49653/292. "A Randomized, Double-Blind, Placebo-Controlled Trial to Assess Three Dose Levels of Rosiglitazone Maleate in the Treatment of Moderate to Severe Plaque Psoriasis," [retrieved from <https://www.gsk-clinicalstudyregister.com/study/49653/292> on Jul. 25, 2017] (3 pages).
Gormin (1989), "Picosecond Transient Absorption Spectra of Aminosalicylates in Confirmation of the Triple Excitation Mechanism," J Phys Chem, 93(16):5979-80.
Guo et al., (2009) "Effect of Uyghur Compound Xipayi Kui Jie' an on the Ultrastructure of Small Intestinal Epithelial Cell in Rat Model of Ulcerative Colitis," J Xinjiang Medi Univ, 32(7):893-4.
Haemmerli U P et al.(1965) "Acquired milk intolerance in the adult caused by lactose malabsorption due to a selective deficiency of intestinal lactase activity," American Journal of Medicine, vol. 38, pp. 7-30.
Harari (2004) "Epidermal Growth Factor Receptor Inhibition Strategies in Oncology," Endocr Relat Cancer, 11(4):689-708.
Harrington LK and Mayberry JF, (2008), 'A Re-appraisal of Lactose Intolerance,' Int J Clin Pract, 62(10):1541-6.
Harrison et al., "Cows' milk protein intolerance: a possible association with gastroenteritis, lacctose intolerance, and IgA deficiency," British Medical Journal 1:1501-1504 (1976).
Highlights of Prescribing Information ACTOS (pioglitazone hydrochloride), Revised Jul. 2011, Retrieved from the Internet (URL): <https://www.accessdata.fda.gov/drugsatfda_docs/label/2011/021073s043s044lbl.pdf>, 43 pages.
Honeder et al. "Improvement of replication fidelity by certain mesalazine derivatives", International Journal of Oncology (2012), 40(5), 1331-1338.
Husova et al., (2007) "Hepatopathy, Coeliac Disease and Lymphocytic Colitis," Ceska A. Slovenska Gastroenterologie A. Hepatologie—CZ SL Gastroenterol Hepatol, 61(6):309-13.
Hyams et al., "Cancer Chemotherapy-Induced Lactose Malabsorption in Children," Cancer 49:646-650 (1982).
International Preliminary Report on Patentability and Written Opinion of the International Searching Authority for PCT/IE2006/000076, dated Jan. 22, 2008 (10 pages).
International Preliminary Report on Patentability and Written Opinion of the International Searching Authority for PCT/EP13/057729, dated Oct. 21, 2014 (6 pages).
International Preliminary Report on Patentability and Written Opinion of the International Searching Authority for PCT/EP2009/008631, dated Jun. 7, 2011(13 pages).
International Preliminary Report on Patentability and Written Opinion of the International Searching Authority for PCT/EP2009/008633, dated Jun. 7, 2011 (6 pages).
International Preliminary Report on Patentability and Written Opinion of the International Searching Authority for PCT/EP2010/000935, dated Aug. 16, 2011 (7 pages).
International Preliminary Report on Patentability and Written Opinion of the International Searching Authority for PCT/EP2010/000939, dated Aug. 16, 2011 (8 pages).
International Preliminary Report on Patentability and Written Opinion of the International Searching Authority for PCT/EP2013/052617, dated Aug. 12, 2014 (5 pages).
International Preliminary Report on Patentability and Written Opinion of the International Searching Authority for PCT/EP2013/069062, dated Mar. 17, 2015 (7 pages).
International Preliminary Report on Patentability and Written Opinion of the International Searching Authority for PCT/EP2013/069063, dated Mar. 17, 2015 (7 pages).
International Preliminary Report on Patentability and Written Opinion of the International Searching Authority for PCT/IE2006/000078, dated Jan. 22, 2008 (14 pages).
International Preliminary Report on Patentability for PCT/EP2008/052354, completed May 22, 2009 (20 pages).
International Preliminary Report on Patentability for PCT/EP2008/068265, completed Apr. 12, 2010 (11 pages).
International Search Report and Written Opinion of the International Searching Authority for International Application No. PCT/EP2017/054526 dated Jun. 2, 2017 (20 pages).
International Search Report and Written Opinion of the International Search Authority for International Application No. PCT/EP2016/071995—dated Jan. 16, 2017 (21 pages total).
International Search Report and Written Opinion of the International Search Authority for International Application No. PCT/EP2017/054526—dated Feb. 6, 2017 (20 pages total).
International Search Report and Written Opinion of the International Searching Authority for International Application No. PCT/EP2016/079512 dated Feb. 28, 2017 (15 pages).

(56) References Cited

OTHER PUBLICATIONS

International Search Report and Written Opinion of the International Searching Authority for PCT/IE2006/000078, dated Jan. 26, 2007 (14 pages).
International Search Report for PCT/EP2008/052354, dated Jun. 9, 2008 (6 pages).
International Search Report for PCT/EP2008/068265, dated Aug. 11, 2009 (5 pages).
International Search Report for PCT/EP2009/008631, dated Aug. 19, 2010 (9 pages).
International Search Report for PCT/EP2009/008633, dated Feb. 22, 2010 (4 pages).
International Search Report for PCT/EP2010/000935 dated Aug. 23, 2010 (5 pages).
International Search Report for PCT/EP2010/000939 dated Sep. 20, 2010 (5 pages).
International Search Report for PCT/EP2013/052617, dated Aug. 12, 2014 (4 pages).
International Search Report for PCT/EP2013/057729, dated Jun. 11, 2013 (4 pages).
International Search Report for PCT/EP2013/069062, dated Dec. 10, 2013 (3 pages).
International Search Report for PCT/EP2013/069063, dated Dec. 20, 2013 (3 pages).
International Search Report for PCT/IE2006/000076, dated Feb. 1, 2007 (5 pages).
Ireland et al., (1992) "Comparison of 5-Aminosalicylic Acid and N-Acetylaminosalicylic Acid Uptake by the Isolated Human Colonic Epithelial Cell," Gut, 33(10):1343-7.
Janda et al., (1988) "Antibody Catalysis of Bimolecular Amide Formation," J Am Chem Soc, 110(14):4835-7.
Jiang J et al., (1997), 'Conjugated Linoleic Acid in Swedish Dairy Products with Special Reference to the Manufacture of Hard Cheeses,' Int Dairy J, 7(12):863-7.
Johnson et al., (2012) 'Intestinal Fibrosis is Reduced by Early Elimination of Inflammation in a Mouse Model of IBD: Impact of a "Top-Down" Approach to Intestinal Fibrosis in Mice,' Inflamm Bowel Dis, 18(3):460-71.
Jones et al., (1997) "Development and Validation of a Genetic Algorithm for Flexible Docking," J Mol Biol, 267(3):727-48.
Julien et al., (2005) 'Antifibrogenic Role of the Cannabinoid Receptor CB2 in the Liver,' Gastroenterology, 128(3):742-55.
Kari et al., (2003) "Targeting the Epidermal Growth Factor Receptor in Cancer: Apoptosis Takes Center Stage," Cancer Res, 63(1):1-5.
Karnik et al., (2009) 'Hair Follicle Stem Cell-specific PPARγ Deletion Causes Scarring Alopecia,' J Invest Dermatol, 129(5):1243-57.
Kermani et al., Mayo Clin Proc. 2003, 78, 1088-1091.
Kloepper et al., (2008) 'Immunophenotyping of the Human Bulge Region: The Quest to Define Useful in situ Markers for Human Epithelial Hair Follicle Stem Cells and their Niche,' Exp Dermatol, 17(7):592-609.
Koeffler, (2003), "Peroxisome Proliferator-activated Receptor γ and Cancers," Clin Cancer Res, 9(1):1-9.
Kuenzli and Saurat, (2003) 'Effect of Topical PPARβ/δ and PPARγ Agonists on Plaque Psoriasis: A Pilot Study,' Dermatology, 206(3):252-6.
Lakshminarayana, N. et al. "Synthesis and evaluation of some novel isochromancarboxylic acid derivatives as potential anti-diabetic agents", European Journal of Medicinal Chemistry (2009), 44(8),3147-3157.
Lavker RM et al., (2003), 'Hair Follicle Stem Cells,' J Investig Dermatol Symp Proc, 8(1):28-38.
Lees et al., (2008) 'Analysis of Germline GLI1 Variation Implicates Hedgehog Signalling in the Regulation of Intestinal Inflammatory Pathways,' PLoS Med, 5(12):e239 (15 pages).
Levi et al., "Synthesis of O-acetyl-?-[N-[p-bis(2-chloroethyl)]-aminophenyl]latic acid ethyl ester," Zhurnal Organicheskoi Khimii (1967), 3(5), 857-61 (Abstract only).

Li et al. "Molecular recognition of nitrated fatty acids by PPARγ" Nat. Struct. Mol. Biol. 2008, 15(8), 865-867.
Li L and Xie T, (2005), 'Stem Cell Niche: Structure and Function,' Annu Rev Cell Dev Biol, 21:605-31.
Liao et al., (1990) 'Therapeutic Effect of Methyl 5-Aminosalicylate on Experimental Ulcerative Colitis in Rabbits,' Acta Pharmacologica Sinica 11(1):54-6.
Lin et al., (1998) "An Antibody Transesterase Derived from Reactive Immunization that Utilizes a Wide Variety of Alcohol Substrates," Chem Commun, 10:1075-6.
Lowe, D. (2009) "More Binding Site Weirdness," CORANTE: In the Pipeline, pp. 1-4.
Lukovac S et al.(2008) "Essential Fatty Acid (EFA) Deficiency in Mice Impairs Lactose Digestion", Abstract M1730, Annual Meeting of the American Gastroenterological Association (AGA) Institute and Digestive Disease Week, May 17-22, 2008, San Diego, CA, Gastroenterology, vol. 134, No. 4, Supplement 1, pp. A-406-A407.
Luna et al. "Oral agents in the management of type 2 diabetes mellitus." Am Fam Physician 63, 1747-1756, 2001 (10 pages).
Lv Chunhua et al. (2009) "Advance on fibrosis in inflammatory bowel disease," Practical Clinical Medicine 10(2):127-129.
Mager et al., (1979) "Struktur-Wirkungs-Beziehungen bei Salizylsaure- und Benzoesaurederivaten," Zbl. Pharm. 118(Heft 12): 1259-75 (concise explanation of relevance attached).
Mandt N et al., (2005), 'Epilation Today: Physiology of the Hair Follicle and Clinical Photo-Epilation,' J Investig Dermatol Symp Proc, 10(3):271-4.
Mangelsdorf et al., (1995) "The Nuclear Receptor Superfamily: The Second Decade," Cell, 83(6):835-9.
Mastrofrancesco, M. et al. "Preclinical Studies of a Specific PPAR? Modulator in the Control of Skin Inflammation," Journal of Investigative Dermatology (2014), 134(4), 1001-1011.
Medline Database, (2013), U.S. National Library of Medicine, Bethesda, MD, XP002763389, Accession No. NLM23651165, Benjamin B et al., 'PPAR-gamma in Ulcerative Colitis: A Novel Target for Intervention,' Curr Drug Targ, 14(12):1501-7.
Medow et al., (1990) 'β-Galactosidase Tablets in the Treatment of Lactose Intolerance in Pediatrics,' Am J Dis Child, 144(11):1261-4 (Abstract).
Meek et al., (1969) "Carboxylation of Substituted Phenols in N,N-Dimethylamide Solvents at Atmospheric Pressure," J Chem Eng Data, 14(3):388-91.
Melgar, et al (2005) "Acute colitis induced by dextran sulfate sodium progresses to chronicity in C57BL6 but not in BALB/c mice: correlation between symptoms and inflammation", American Journal of Physiology—Gastrointestinal and Liver Physiology, vol. 288, No. 6, pp. G1328-G1338, XP055433729.
Mendelsohn (2001) "The Epidermal Growth Factor Receptor as a Target for Cancer Therapy," Endocr Relat Cancer, 8(1):3-9.
Merck Manual Home Edition, "Ulcerative Colitis", Merck Sharp & Dohme Corp., Copyright @ 2004-2011, pp. 1-6 [online] [retrieved on Apr. 19, 2013] Retrieved from http://www.merckmanuals.com/home/print/digestive_disorders/inflammatory_bowel_diseases_ibd/ulcerative_colitis.html.
Michalik and Wahli, (2007) 'Peroxisome Proliferator-activated Receptors (PPARs) in Skin Health, Repair and Disease,' Biochim Biophys Acta, 1771(8):991-8.
Mirmirani and Karnik, (2009), 'Lichen Planopilaris Treated with a Peroxisome Proliferator-Activated Receptor γ Agonist,' Arch Dermatol, 145(12):1363-6 [NIH Public Access Author Manuscript].
Misra et al., (2002) "Phosphorylation of Transcriptional Coactivator Peroxisome Proliferator-Activated Receptor (PPAR)-Binding Protein (PBP). Stimulation of Transcriptional Regulation by Mitogen-Activated Protein Kinase," J Biol Chem, 277(50): 48745-54.
Nesto, R.W et al., AHA/ADA Consensus Statement dated Dec. 9, 2003, pp. 2941-2948.
Nolte et al., (1998) "Ligand Binding and Co-Activator Assembly of the Peroxisome Proliferator-Activated Receptor-γ," Nature, 395(6698):137-43.
O'Mahony, et al., (1990) "Coeliac Disease and Collagenous Colitis," Postgrad Med, 66(773):238-41.

(56) References Cited

OTHER PUBLICATIONS

Office Action issued in Japanese Patent Application No. 2011-549494 dated Feb. 25, 2014, with English language translation (8 pages).
Osawa et al., (2003) "Peroxisome Proliferator-Activated Receptor γ Ligands Suppress Colon Carcinogenesis Induced by Azoxymethane in Mice," Gastroenterology, 124(2):361-7.
Oshima H et al., (2001), 'Morphogenesis and Renewal of Hair Follicles from Adult Multipotent Stem Cells,' Cell, 104(2):233-45.
Patricia J. Sime (2007) "Exploring the peroxisome proliferator activated receptor gamma (PPARγ) pathway as a novel thereapy for lung fibrosis," Seminar of Integrated Traditional Chinese and Western Experimental Medicine pp. 36-38.
PCT/EP2020/053369 International Search Report and Written Opinion dated Apr. 20, 2020.
Pedersen et al., (2010) 'Topical Rosiglitazone Treatment Improves Ulcerative Colitis by Restoring Peroxisome Proliferator-Activated Receptor-γ Activity,' Am J Gastroenterol, 105(7):1596-1603 (Abstract).
Pershadsingh et al., (2005) 'Improvement in Psoriasis with Rosiglitazone in a Diabetic and a Nondiabetic Patient,' Skinmed, 4(6):386-90 (Abstract).
Peyrin-Biroulet et al., (2010), 'Peroxisome Proliferator-Activated Receptor Gamma Activation is Required for Maintenance of Innate Antimicrobial Immunity in the Colon,' Proc Natl Acad Sci USA, 107(19):8772-7.
Peyrin-Biroulet, et al. (2007) "Peroxisome Proliferator-Activated Receptor Gamma Functions as an Antibacterial Factor," J Crohns Colitis Suppl, 1(1):2.
Ponchant et al., (1991) Synthesis of 5-[$^{125}$I]-Iodo-Zacopride, a New Probe for 5-HT$_3$ Receptor Binding Sites, Journal of Labelled Compounds and Radiopharmaceuticals, 29(10):1147-55.
Porter and Ihrig, (1923), 'Asymmetric Dyes,' J Am Chem Soc, 45(8):1990-3 (Abstract only).
Ramprasad et al., (2002) 'Sustained-Delivery of Apolipoprotein E-peptidomimetic Using Multivesicular Liposomes Lowers Serum Cholesterol Levels,' J Control Release, 79(1-3):207-18.
Rathi, (2011), 'Acne Vulgaris Treatment: The Current Scenario,' Indian J Dermatol, 56(1):7-13.
Reifen, Ram, et al. (2004) "5-ASA and Lycopene Decrease the Oxidative Stress and Inflammation Induced by Iron in Rats with Colitis," J Gastroenterol, 3996):514-9.
Result Summary for Study ID No. SB-999910/150 (2002) "A Study in Patients with Crohn's Disease to Evaluate the Effect of AVANDIA™ on Inflammatory Activity Mediated by Monocytes/Macrophages" Retrieved from: download.gsk-clinicalstudyregister.com/files/23093.pdf on May 23, 2012 (2 pages).
Risérus et al., (2008) "Activation of Peroxisome Proliferator-activated Receptor (PPAR) Delta Promotes Reversal of Multiple Metabolic Abnormalities, Reduces Oxidative Stress, and Increases Fatty Acid Oxidation in Moderately Obese Men," Diabetes, 57(NR. 2):332-9.
Ritland et al., (1999) 'Evaluation of 5-Aminosalicylic Acid (5-ASA) for Cancer Chemoprevention: Lack of Efficacy against Nascent Adenomatous Polyps in the Apc$^{Min}$ Mouse,' Clin Cancer Res, 5(4):855-63.
Robertson et al., (1985) 'Structure-Activity Relationships of Arylimidazopyridine Cardiotonics: Discovery and Inotropic Activity of 2-[2-Methoxy-4-(methylsulfinyl)phenyl]-1H-imidazo[4,5-c]pyridine,' J Med Chem, 28(6):717-27.
Rousseaux et al., (2005) "Intestinal Anti-inflammatory Effect of 5-Aminosalicylic Acid is Dependent on Peroxisome Proliferator-Activated Receptor-γ," J Exp Med, 201(8):1205-15.
Rousseaux et al., (2010), 'Preclinical and Toxicological Assessments of the Novel Orally Bioavailable PPAR Ligand GED-0507-34-Levo for the Treatment of Inflammatory Bowel Disease,' Gastroenterology 2010 DDW Abstract Supplement, AGA Abstract #1080, 138(5-Suppl 1):S-157.

Rousseaux et al., (2011) 'Preclinical Evaluation of Intestinal Anti-Inflammatory/Analgesic Properties and Phase I Clinical Trial of a New PPAR Agonist Ged-0507-34-Levo,' Gastroenterology, 140(5):S-515 (Abstract).
Rovner (2009) "An Enzyme Reveals an Unexpected Inclusiveness, Protein Binding: Bacterial Enzyme's Active Site Welcomes Both Enantiomers of a Chiral Molecule at the Same Time," Chem Eng News, Nov. 5, 2009 issue, (2 pages) retieved from http://cen.acs.org/articles/87/web/2009/11/Enzyme-Reveals-Unexpected-Inclusiveness.html?type=paidArticleContent.
Schauber J et al., (2004) 'Histone-Deacetylase Inhibitors Induce the Cathelicidin LL-37 in Gastrointestinal Cells,' Mol Immunol, 41(9):847-54.
Schwab et al., (2007) 'Role of Nuclear Hormone Receptors in Butyrate-Mediated Up-Regulation of the Antimicrobial Peptide Cathelicidin in Epithelial Colorectal Cells,' Mol Immunol, 44(8):2107-14.
Sherwin (1924), "Acetylation as a Physiologic Reaction," Proc Soc Exper Biol & Med, 22:182.
Speca et al., (2012) 'Cellular and Molecular Mechanisms of Intestinal Fibrosis,' World J Gastroenterol, 18(28):3635-61.
Tanaka et al., (2001) "Ligands for Peroxisome Proliferator-Activated Receptors α and γ Inhibit Chemically Induced Colitis and Formation of Aberrant Crypt Foci in Rats," Cancer Res., 61(6):2424-8.
The International Search Report and The Written Opinion of the International Searching Authority for International Application No. PCT/EP2017/054526 dated Jun. 2, 2017 (20 pages).
Tosti et al., (2009) 'Treatment Strategies for Alopecia,' Expert Opin Pharmacother, 10(6):1017-26.
Troilius A and Troilius C, (1999), 'Hair Removal with a Second Generation Broad Spectrum Intense Pulsed Light Source—A Long Term Follow-up,' J Cutan Laser Ther, 1(3):173-8.
Tuleu, et al., (2002) "Colonic Delivery of 4-Aminosalicylic Acid Using Amylose-Ethyl Cellulose-Coated Hydroxypropyl Methyl Cellulose Capsules," Aliment Pharmacol Ther., 167(10):1771-9.
Tursi et al., (2002), 'Long-Term Treatment with Mesalazine and Rifaximin Versus Rifaximin Alone for Patients with Recurrent Attacks of Acute Diverticulitis of Colon,' Digest Liver Dis, 34(7):510-5.
Tursi, (2004), 'Acute Diverticulitis of the Colon—Current Medical Therapeutic Management,' Exp Opin Pharmacother, 5(1):55-9.
Tzameli et al., (2004) 'Regulated Production of a Peroxisome Proliferator-Activated Receptor-γ Ligand During an Early Phase of Adipocyte Differentiation in 3T3-L1 Adipocytes,' J Biol Chem, 279(34):36093-102.
Van't Riet, Bart, et al. (1979) "Synthesis of Hydroxy and Amino-Substituted Benzohydroxamic Acids: Inhibition of Ribonucleotide Reductase and Antitumor Activity," J Med Chem, 22(5) 589-92.
Venkatraman et al., (2004) 'Alpha-Lipoic Acid-Based PPARγ Agonists for Treating Inflammatory Skin Diseases,' Arch Dermatol Res, 296(3):97-104 (Abstract).
Wallace et al., (1989) 'Inhibition of Leukotriene Synthesis Markedly Accelerates Healing in Rat Model of Inflammatory Bowel Disease,' Gastroenterology, 96(1):29-36.
Wang et al., (2002) "Further Development and Validation of Emphirical Scoring Functions for Structure-Based Binding Affinity Prediction," J Comput Aided Mol Des, 16(1):11-26.
Wang et al., (2004) 'Cutting Edge: 1,25-Dihydroxyvitamin D3 is a Direct Inducer of Antimicrobial Peptide Gene Expression,' J Immunol, 173(5):2909-12.
Wei et al., (2010) 'Peroxisome Proliferator-Activated Receptor γ: Innate Protection from Excessive Fibrogenesis and Potential therapeutic Target in Systemic Sclerosis,' Curr Opin Rheumatol, 22(6):671-6 (HHS Public Access version of Author Manuscript).
Westin et al., (1998) "Interactions Controlling the Assembly of Nuclear-Receptor Heterodimers and Co-Activators," Nature, 395(6698):199-202.
Williams and Hallett (1989) "Effect of Sulphasalazine and its Active Metabolite, 5-Amino-Salicylic Acid, on Toxic Oxyden Metabolite Production by Neutrophils," Gut, 30(11):1581-7.

(56) References Cited

OTHER PUBLICATIONS

Written Opinion of International Searching Authority and and International Search Report issued in PCT/EP2020/051810 dated May 5, 2020 (12 pages).
Written Opinion of International Searching Authority and International Search Report issued in International application No. PCT/EP2020/053369 dated Apr. 20, 2020 (10 pages).
Written Opinion of the International Searching Authority for International Application No. PCT/EP2008/052354 dated Jun. 9, 2008 (10 pages).
Written Opinion of the International Searching Authority for International Application No. PCT/EP2008/068265 dated Aug. 11, 2009 (12 pages).
Written Opinion of the International Searching Authority for International Application No. PCT/EP2013/052617 dated Aug. 12, 2014 (4 pages).
Written Opinion of the International Searching Authority for International Application No. PCT/EP2013/069062 dated Dec. 10, 2013 (6 pages).
Written Opinion of the International Searching Authority for International Application No. PCT/EP2013/069063 dated Dec. 29, 2013 (7 pages).
Written Opinion of the International Searching Authority for International Application No. PCT/IE2006/000076 dated Feb. 1, 2007 (9 pages).
Wu et al., (2006) 'Effects of Rosiglitazone on Expression of TGF-A1 in Experimental Hepatic Fibrosis Rats,' Chin J Gastroenterol Hepatol, 15(2):126-9.
Xu et al., (2001) "Structural Determinants of Ligand Binding Selectivity Between the Peroxisome Proliferator-Activated Receptors," Proc Natl Acad Sci USA, 98(24):13919-24.
Yanai et al., (2004) "Para-Position Derivatives of Fungal Anthelmintic Cyclodepsipeptides Engineered with Streptomyces Venezuelae Antibiotic Biosynthetic Genes," Nat Biotechnol, 22(7):848-55.
Ye; "Regulation of PPARγ function by TNF-a"; 2008; Biochemical and Biophysical Research Communications; 374: 405-408 (Year: 2008).
Youssef and Badr, (2004) "Role of Peroxisome Proliferator-Activated Receptors in Inflammation Control," J Biomed Biotechnol, 2004(3):156-66.
Yu et al., (2010) 'Peroxisome Proliferator-Activated Receptors Gamma Reverses Hepatic Nutritional Fibrosis in Mice and Suppresses Activation of Hepatic Stellate Cells in vitro,' Int J Biochem Cell Biol, 42(6):948-57.
Zhou et al., (1999) 'Intestinal Metabolism and Transport of 5-Aminosalicylate,' Drug Metab Dispos, 27(4):479-85.
U.S. Appl. No. 15/088,654, Methods for Preventing or Reducing Colon Carcinogenesis, filed Apr. 1, 2016, U.S. Pat. No. 9,913,817.
U.S. Appl. No. 13/201,786, Alkylamido Compounds and Uses Thereof, filed Nov. 17, 2011, U.S. Pat. No. 8,754,127.
U.S. Appl. No. 14/255,255, Alkylamido Compounds and Uses Thereof, filed Apr. 17, 2014, U.S. Pat. No. 9,511,041.
U.S. Appl. No. 15/337,707, Alkylamido Compounds and Uses Thereof, filed Oct. 28, 2016, U.S. Pat. No. 10,137,101.
U.S. Appl. No. 17/539,447, Alkylamido Compounds and Uses Thereof, filed Dec. 1, 2021, Pending.
U.S. Appl. No. 13/131,982, Methods of Preventing or Reducing Colon Carcinogenesis, filed Aug. 11, 2011, U.S. Pat. No. 8,501,806, Abandoned.
U.S. Appl. No. 13/201,790, Methods of Treating Hair Related Conditions, filed Nov. 17, 2011, U.S. Pat. No. 8,796,334.
U.S. Appl. No. 14/969,939, Methods of Treating Hair Related Conditions, filed Dec. 15, 2015, U.S. Pat. No. 9,901,557.
U.S. Appl. No. 15/872,436, Methods of Treating Hair Related Conditions, filed Jan. 16, 2018, U.S. Pat. No. 10,398,667.
U.S. Appl. No. 16/515,532, Methods of Treating Hair Related Conditions, filed Jul. 18, 2019, U.S. Pat. No. 10,959,970.
U.S. Appl. No. 11/989,090, Compounds and Their Salts Specific to the PPAR Receptors and the EGF Receptors and Their Use in the Medical Field, filed Jun. 6, 2008, U.S. Pat. No. 8,153,841.
U.S. Appl. No. 13/408,439, Compounds and Their Salts Specific to the PPAR Receptors and the EGF Receptors and Their Use in the Medical Field, filed Feb. 29, 2012, U.S. Pat. No. 8,710,100.
U.S. Appl. No. 14/202,386, Compounds and Their Salts Specific to the PPAR Receptors and the EGF Receptors and Their Use in the Medical Field, filed Mar. 10, 2014, U.S. Pat. No. 9,133,099.
U.S. Appl. No. 14/671,579, Compounds and Their Salts Specific to the PPAR Receptors and the EGF Receptors and Their Use in the Medical Field, filed Mar. 27, 2015, U.S. Pat. No. 9,561,202.
U.S. Appl. No. 15/377,013, Compounds and Their Salts Specific to the PPAR Receptors and the EGF Receptors and Their Use in the Medical Field, filed Dec. 13, 2016, U.S. Pat. No. 10,016,381.
U.S. Appl. No. 14/671,585, Compounds and Their Salts Specific to the PPAR Receptors and the EGF Receptors and Their Use in the Medical Field, filed Mar. 27, 2015, U.S. Pat. No. 9,345,680.
U.S. Appl. No. 11/989,033, Compounds and Their Salts Specific to the PPAR Receptors and EGF Receptors and Their Use in the Medical Field, filed Jun. 6, 2008, U.S. Pat. No. 8,138,357.
U.S. Appl. No. 13/397,245, Compounds and Their Salts Specific to the PPAR Receptors and EGF Receptors and Their Use in the Medical Field, filed Feb. 15, 2012, U.S. Pat. No. 8,450,506.
U.S. Appl. No. 12/810,159, Compounds for the Selective Treatment of the Intestinal Immuno-Inflammatory Component of the Celiac Disease, filed Aug. 16, 2010, U.S. Pat. No. 8,153,693.
U.S. Appl. No. 14/377,362, Methods of Treating Fibrosis, filed Aug. 7, 2014, U.S. Pat. No. 9,682,923.
U.S. Appl. No. 15/593,864, Methods of Treating Fibrosis, filed May 12, 2017, U.S. Pat. No. 11,046,641.
U.S. Appl. No. 17/199,860, Methods of Treating Fibrosis, filed Mar. 12, 2021, Published US 2022/0033346.
U.S. Appl. No. 14/394,916, Methods of Treating Lactose Intolerance, filed Oct. 16, 2014, U.S. Pat. No. 9,682,050.
U.S. Appl. No. 16/078,555, Methods of Treating Lactose Intolerance, filed Aug. 21, 2018, Published US 2019/0046490.
U.S. Appl. No. 17/425,648, Compositions for Use in Preventing Acne, filed Jul. 23, 2021, Published US 2022/0000818.

\* cited by examiner

PROCESS OF MAKING 3-(4'-AMINOPHENYL)-2-METHOXYPROPIONIC ACID, AND ANALOGS AND INTERMEDIATES THEREOF

CROSS-REFERENCE TO RELATED APPLICATIONS

This application is a U.S. national stage patent application under 35 U.S.C. § 371 of International Application No. PCT/EP2020/053369, filed on Feb. 10, 2020, which application claims the benefit of and priority to U.S. Provisional Application No. 62/802,802, filed on Feb. 8, 2019, each of which is incorporated by reference herein in its entirety.

BACKGROUND

Peroxisome Proliferator Activated Receptors (PPARs) are members of the nuclear hormone receptor super family, which are ligand-activated transcription factors regulating gene expression. Certain PPARs play roles in the regulation of cell differentiation, development and metabolism of higher organisms.

Three types of PPAR have been identified: alpha, expressed in the liver, kidney, heart and other tissues and organs, beta/delta expressed, for example, in the brain, and gamma, expressed in three forms: gamma1, gamma2, and gamma3. PPARγ receptors have been associated with a number of disease states including fibrotic diseases, dyslipidemia, hyperlipidemia, hypercholesteremia, atherosclerosis, atherogenesis, hypertriglyceridemia, heart failure, myocardial infarction, vascular diseases, cardiovascular diseases, hypertension, obesity, inflammation, arthritis, cancer, Alzheimer's disease, skin disorders, respiratory diseases, ophthalmic disorders, IBDs (irritable bowel disease), ulcerative colitis and Crohn's disease.

Further, treatment of tumor cells with ligands of PPARγ receptors can induce a decrease in cellular proliferation, cell differentiation and apoptosis, and therefore may be useful in preventing carcinogenesis. Intestinal anti-inflammatory activity may be dependent on binding and subsequent activation of PPARγ receptors.

Accordingly, effective processes for making compounds capable of modulating the activity of PPARs receptors are needed to address the treatment of such diseases.

SUMMARY

The disclosure provides, for example, a process for the preparation of compounds which may be modulators of PPARs receptors.

The present disclosure provides, in part, a process for the preparation of a compound of Formula (VII):

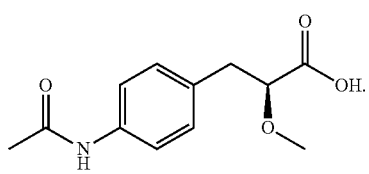

(VII)

One embodiment provides a process for preparing of a compound of Formula (VI):

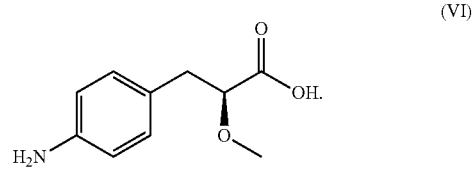

(VI)

Also contemplated herein is a process for the preparation of analogs and intermediates thereof.

In one embodiment, at least some of the compounds identified as intermediates e.g., as part of a synthetic scheme disclosed herein are contemplated as compounds of the disclosure, e.g., a compound represented by Formula (I) or a pharmaceutically acceptable salt or stereoisomer thereof:

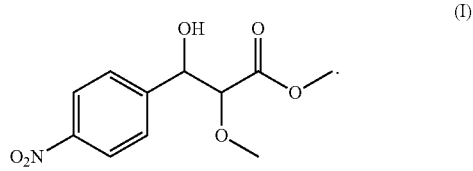 [SMILES: COC(=O)C(OC)C(O)c1ccc([N+](=O)[O-])cc1]

(I)

DETAILED DESCRIPTION

The features and other details of the disclosure will now be more particularly described. Before further description of the present disclosure, certain terms employed in the specification, examples and appended claims are collected here. These definitions should be read in light of the remainder of the disclosure and understood as by a person of skill in the art. Unless defined otherwise, all technical and scientific terms used herein have the same meaning as commonly understood by a person of ordinary skill in the art.

Definitions

The term "alkenyl" as used herein refers to an unsaturated straight or branched hydrocarbon having at least one carbon-carbon double bond, such as a straight or branched group of 2-12, 2-10, or 2-6 carbon atoms, referred to herein as $C_2$-$C_{12}$alkenyl, $C_2$-$C_{10}$alkenyl, and $C_2$-$C_6$alkenyl, respectively. Exemplary alkenyl groups include, but are not limited to, vinyl, allyl, butenyl, pentenyl, hexenyl, butadienyl, pentadienyl, hexadienyl, 2-ethylhexenyl, 2-propyl-2-butenyl, 4-(2-methyl-3-butene)-pentenyl, etc.

The term "alkoxy" as used herein refers to an alkyl group attached to an oxygen (—O-alkyl). Exemplary alkoxy groups include, but are not limited to, groups with an alkyl, alkenyl or alkynyl group of 1-12, 1-8, or 1-6 carbon atoms, referred to herein as $C_1$-$C_{12}$alkoxy, $C_1$-$C_8$alkoxy, and $C_1$-$C_6$alkoxy, respectively. Exemplary alkoxy groups include, but are not limited to methoxy, ethoxy, etc. Similarly, exemplary "alkenoxy" groups include, but are not limited to vinyloxy, allyloxy, butenoxy, etc.

The term "alkyl" as used herein refers to a saturated straight or branched hydrocarbon, such as a straight or branched group of 1-12, 1-10, 1-6, 1-4, or 1-3 carbon atoms, referred to herein as $C_1$-$C_{12}$alkyl, $C_1$-$C_{10}$alkyl, $C_1$-$C_6$alkyl, $C_{1-4}$alkyl, and $C_{1-3}$alkyl respectively. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl- 1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, octyl, etc. In certain embodiments, alkyl refers to $C_1$-$C_6$ alkyl. In certain embodiments, cycloalkyl refers to $C_3$-$C_6$cycloalkyl.

Alkyl, alkenyl and alkynyl groups can, in some embodiments, be optionally be substituted with or interrupted by at least one group selected from alkanoyl, alkoxy, alkyl, alkenyl, alkynyl, amido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl and thiocarbonyl.

The term "alkynyl" as used herein refers to an unsaturated straight or branched hydrocarbon having at least one carbon-carbon triple bond, such as a straight or branched group of 2-12, 2-8, or 2-6 carbon atoms, referred to herein as $C_2$-$C_{12}$alkynyl, $C_2$-$C_8$alkynyl, and $C_2$-$C_6$alkynyl, respectively. Exemplary alkynyl groups include, but are not limited to, ethynyl, propynyl, butynyl, pentynyl, hexynyl, methylpropynyl, 4-methyl-1-butynyl, 4-propyl-2-pentynyl, and 4-butyl-2-hexynyl, etc.

The term "amide" or "amido" as used herein refers to a radical of the form —$R_aC(O)N(R_b)$—, —$R_aC(O)N(R_b)R_c$—, or —$C(O)NR_bR_c$, wherein $R_a$, $R_b$ and $R_c$ are each independently selected from alkyl, alkenyl, alkynyl, aryl, arylalkyl, cycloalkyl, heteroaryl, heterocyclyl, and hydrogen. The amide can be attached to another group through the carbon, the nitrogen, $R_b$, $R_c$, or $R_a$. The amide also may be cyclic, for example $R_b$ and $R_c$, $R_a$ and $R_b$, or $R_a$ and $R_c$ may be joined to form a 3- to 12-membered ring, such as a 3- to 10-membered ring or a 5- to 6-membered ring.

The term "amidino" as used herein refers to a radical of the form —$C(=NR)NR'R''$ where R, R', and R'' can each independently be selected from alkyl, alkenyl, alkynyl, aryl, arylalkyl, cycloalkyl, heteroaryl, and heterocyclyl.

The term "amine" or "amino" as used herein refers to a radical of the form —$NR_dR_e$, —$N(R_d)R_e$—, or —$R_eN(R_d)R_f$— where $R_d$, $R_e$, and $R_f$ are independently selected from alkyl, alkenyl, alkynyl, aryl, arylalkyl, cycloalkyl, haloalkyl, heteroaryl, heterocyclyl, and hydrogen. The amino can be attached to the parent molecular group through the nitrogen, $R_d$, $R_e$ or $R_f$. The amino also may be cyclic, for example any two of $R_d$, $R_e$ or $R_f$ may be joined together or with the N to form a 3- to 12-membered ring, e.g., morpholino or piperidinyl. The term amino also includes the corresponding quaternary ammonium salt of any amino group, e.g., —$[N(R_d)(R_e)(R_f)]^+$. Exemplary amino groups include aminoalkyl groups, wherein at least one of $R_d$, $R_e$, or $R_f$ is an alkyl group.

The term "aryl" as used herein refers to a mono-, bi-, or other multi-carbocyclic, aromatic ring system. In certain embodiments, aryl refers to a monocyclic and/or bicyclic, 6 to 10 membered ring. The aromatic ring may be substituted at one or more ring positions with substituents selected from alkanoyl, alkoxy, alkyl, alkenyl, alkynyl, amido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl and thiocarbonyl. The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, and/or aryls. Exemplary aryl groups include, but are not limited to, phenyl, tolyl, anthracenyl, fluorenyl, indenyl, azulenyl, and naphthyl, as well as benzo-fused carbocyclic moieties such as 5,6,7,8-tetrahydronaphthyl.

The term "arylalkyl" as used herein refers to an aryl group having at least one alkyl substituent, e.g., -aryl-alkyl. Exemplary arylalkyl groups include, but are not limited to, arylalkyls having a monocyclic aromatic ring system, wherein the ring comprises 6 carbon atoms. For example, "phenylalkyl" includes phenyl$C_4$alkyl, benzyl, 1-phenylethyl, 2-phenylethyl, etc.

The term "carbonyl" as used herein refers to the radical —$C(O)$—.

The term "carboxy" as used herein refers to the radical —COOH or its corresponding salts, e.g., —COONa, etc.

The term "cyano" as used herein refers to the radical —CN.

The term "cycloalkyl" as used herein refers to a monovalent saturated or unsaturated cyclic, bicyclic, or bridged bicyclic hydrocarbon group of 3-12, 3-8, 4-8, or 4-6 carbons, referred to herein, e.g., as "$C_{4-8}$cycloalkyl," derived from a cycloalkane. Exemplary cycloalkyl groups include, but are not limited to, cyclohexanes, cyclohexenes, cyclopentanes, cyclopentenes, cyclobutanes and cyclopropanes. Cycloalkyl groups may be substituted with alkanoyl, alkoxy, alkyl, alkenyl, alkynyl, amido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl and thiocarbonyl. Cycloalkyl groups can be fused to other cycloalkyl, aryl, or heterocyclyl groups. In certain embodiments, cycloalkyl refers to $C_3$-$C_6$ alkyl.

The terms "halo" or "halogen" as used herein refer to F, Cl, Br, or I.

The term "haloalkyl" as used herein refers to an alkyl group substituted with one or more halogen atoms.

The term "nitro" as used herein refers to the radical —$NO_2$.

The term "phenyl" as used herein refers to a 6-membered carbocyclic aromatic ring. The phenyl group can also be fused to a cyclohexane or cyclopentane ring. Phenyl can be substituted with one or more substituents including alkanoyl, alkoxy, alkyl, alkenyl, alkynyl, amido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl and thiocarbonyl.

The term "phosphate" as used herein refers to the radical —$OP(O)(OR_{aa})_2$ or its anions. The term "phosphonate" refers to the radical —$P(O)(OR_{aa})_2$ or its anions. The term "phosphinate" refers to the radical —$PR_{aa}(O)(OR_{aa})$ or its anion, where each $R_{aa}$ can be selected from, for example, alkyl, alkenyl, alkynyl, aryl, arylalkyl, cycloalkyl, hydrogen, haloalkyl, heteroaryl, and heterocyclyl.

The term "pharmaceutically acceptable carrier" or "pharmaceutically acceptable excipient" as used herein refers to any and all solvents, dispersion media, coatings, isotonic and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions.

The term "pharmaceutical composition" as used herein refers to a composition comprising at least one compound as disclosed herein formulated together with one or more pharmaceutically acceptable carriers.

The term "pharmaceutically acceptable salt(s)" as used herein refers to salts of acidic or basic groups that may be present in compounds used in the present compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including but not limited to malate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that include an amino moiety may form pharmaceutically acceptable salts with various amino acids, in addition to the acids mentioned above. Compounds included in the present compositions that are acidic in nature are capable of forming base salts with various pharmacologically acceptable cations. Examples of such salts include alkali metal or alkaline earth metal salts and, particularly, calcium, magnesium, sodium, lithium, zinc, potassium, and iron salts.

The compounds of the disclosure may contain one or more stereogenic centers and/or double bonds and, therefore, exist as stereoisomers, such as geometric isomers, enantiomers or diastereomers. The term "stereoisomers" when used herein consist of all geometric isomers, enantiomers or diastereomers. These compounds may be designated by the symbols "R" or "S," depending on the configuration of substituents around the stereogenic carbon atom. The present disclosure encompasses various stereoisomers of these compounds and mixtures thereof. Stereoisomers include enantiomers and diastereomers. Mixtures of enantiomers or diastereomers may be designated "(±)" in nomenclature, but the skilled artisan will recognize that a structure may denote a chiral center implicitly.

Individual stereoisomers of compounds of the present disclosure can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, or (3) direct separation of the mixture of optical enantiomers on chiral chromatographic columns. Stereoisomeric mixtures can also be resolved into their component stereoisomers by well-known methods, such as chiral-phase gas chromatography, chiral-phase high performance liquid chromatography, crystallizing the compound as a chiral salt complex, or crystallizing the compound in a chiral solvent. Stereoisomers can also be obtained from stereomerically-pure intermediates, reagents, and catalysts by well-known asymmetric synthetic methods.

Geometric isomers can also exist in the compounds of the present disclosure. The symbol ═ denotes a bond that may be a single, double or triple bond as described herein. The present disclosure encompasses the various geometric isomers and mixtures thereof resulting from the arrangement of substituents around a carbon-carbon double bond or arrangement of substituents around a carbocyclic ring. Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers.

Substituents around a carbon-carbon double bond alternatively can be referred to as "cis" or "trans," where "cis" represents substituents on the same side of the double bond and "trans" represents substituents on opposite sides of the double bond. The arrangement of substituents around a carbocyclic ring are designated as "cis" or "trans." The term "cis" represents substituents on the same side of the plane of the ring and the term "trans" represents substituents on opposite sides of the plane of the ring. Mixtures of compounds wherein the substituents are disposed on both the same and opposite sides of plane of the ring are designated "cis/trans."

The term "substantially optically pure", "substantially enantiomerically pure", "optically pure" or "enantiomerically pure" as used herein when referring to a compound (e.g., a compound described herein) means that at least 95%, for example, at least 96%, at least 97%, or at least 98% of the compound has the desired stereogenic center in a given configuration. It will be appreciated that the percentage is expressed as a percentage of both enantiomers of the compound. For example, a compound of Formula VII is substantially optically pure if, based on the total of both the levorotatory and dextrorotatory enantiomers, at least 95% is (S)—(−)-3-(4-acetamidophenyl)-2-methoxypropionic acid (the levorotatory enantiomer).

The compounds disclosed herein can exist in solvated as well as unsolvated forms with pharmaceutically acceptable solvents such as water, ethanol, and the like, and it is intended that the disclosure embrace both solvated and unsolvated forms. In some embodiments, the compound is amorphous. In some embodiments, the compound is in a crystalline form. In some embodiments, the compound is a polymorph.

The disclosure also embraces isotopically labeled compounds of the disclosure which are identical to those recited herein, except that one or more atoms are replaced by an atom having an atomic mass or mass number different from the atomic mass or mass number usually found in nature. Examples of isotopes that can be incorporated into compounds of the disclosure include isotopes of hydrogen, carbon, nitrogen, oxygen, phosphorus, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Certain isotopically-labeled disclosed compounds (e.g., those labeled with $^{3}H$ and $^{14}C$) are useful in compound and/or substrate tissue distribution assays. Tritiated (i.e., $^{3}H$) and carbon-14 (i.e., $^{14}C$) isotopes are particularly preferred for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Isotopically labeled compounds of the disclosure can generally be prepared by following procedures analogous to those disclosed in the e.g., Examples herein by substituting an isotopically labeled reagent for a non-isotopically labeled reagent.

The term "prodrug" refers to compounds that are transformed in vivo to yield a disclosed compound or a pharmaceutically acceptable salt, hydrate or solvate of the compound. The transformation may occur by various mechanisms, such as through hydrolysis in blood. For example, if a compound of the disclosure or a pharmaceutically acceptable salt, hydrate or solvate of the compound contains a carboxylic acid functional group, a prodrug can comprise an ester formed by the replacement of the hydrogen atom of the acid group with a group such as ($C_1$-$C_8$) alkyl, ($C_2$-$C_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di($C_1$-$C_2$)alkylcarbamoyl-($C_1$-$C_2$)alkyl and piperidino-, pyrrolidino- or morpholino($C_2$-$C_3$)alkyl.

Similarly, if a compound of the disclosure contains an alcohol functional group, a prodrug can be formed by the replacement of the hydrogen atom of the alcohol group with a group such as ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl ($C_1$-$C_6$)alkoxycarbonyloxymethyl, N—($C_1$-$C_6$)alkoxycarbonylaminomethyl, succinoyl, ($C_1$-$C_6$)alkanoyl, α-amino ($C_1$-$C_4$)alkanoyl, arylacyl and α-aminoacyl, or α-aminoacyl-α-aminoacyl, where each α-aminoacyl group is independently selected from the naturally occurring L-amino acids, $P(O)(OH)_2$, —$P(O)(O(_{C1}$-$C_6)alkyl)_2$ or glycosyl (the radical resulting from the removal of a hydroxyl group of the hemiacetal form of a carbohydrate).

If a compound of the disclosure incorporates an amine functional group, a prodrug can be formed by the replacement of a hydrogen atom in the amine group with a group such as R-carbonyl, RO-carbonyl, NRR'-carbonyl where R and R' are each independently ($C_1$-$C_{10}$)alkyl, ($C_3$-$C_7$)cycloalkyl, benzyl, or R-carbonyl is a natural α-aminoacyl or natural α-aminoacyl-natural α-aminoacyl, —C(OH)C(O)$OY^1$ wherein $Y^1$ is H, ($C_1$-$C_6$)alkyl or benzyl, —$C(OY^2)Y^3$ wherein $Y^2$ is ($C_2$-$C_4$) alkyl and $Y^3$ is ($C_1$-$C_6$)alkyl, carboxy ($C_1$-$C_6$)alkyl, amino($C_1$-$C_4$)alkyl or mono-N— or di-N,N—($C_1$-$C_6$)alkylaminoalkyl, —$C(Y^4)Y^5$ wherein $Y^4$ is H or methyl and $Y^5$ is mono-N— or di-N,N—($C_1$-$C_6$)alkylamino, morpholino, piperidin-1-yl or pyrrolidin-1-yl.

The disclosure provides, at least in part, compounds represented by Formula (I), Formula (IV), Formula (V), Formula (VI), and Formula (VII), as depicted below. Also contemplated herein are pharmaceutical compositions that include a compound represented by Formula (I), Formula (IV), Formula (V), Formula (VI), and Formula (VII), and e.g., a pharmaceutically acceptable excipient and/or carrier.

Compounds

Provided herein in part is a process for preparing a substantially optically pure compound of Formula (VII):

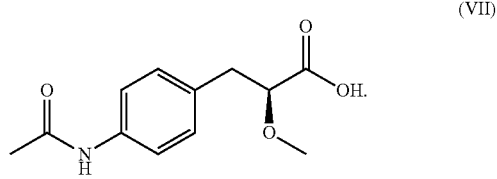 [SMILES: CO[C@@H](Cc1ccc(NC(C)=O)cc1)C(=O)O]

the process comprising:
reacting a compound of Formula (I):

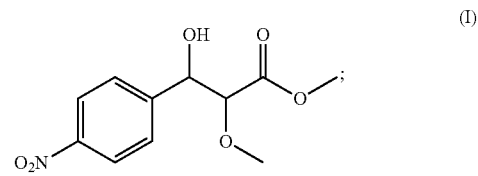 [SMILES: COC(=O)C(OC)C(O)c1ccc([N+](=O)[O-])cc1]

with an activating agent, in the optional presence of a base, to form an intermediate of Formula (I-A):

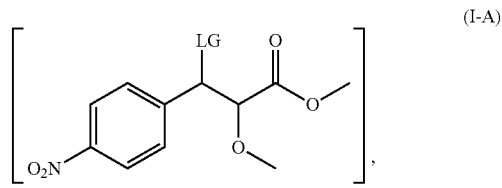

wherein LG is a leaving group;
treating the intermediate of Formula (I-A) with a base solution in the presence of an alcohol solvent, to eliminate the leaving group and thereby forming an intermediate of Formula (I-B):

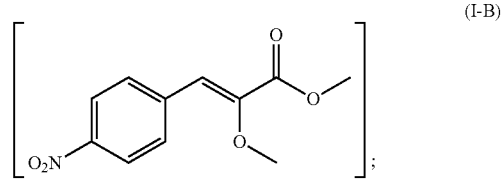

hydrolyzing the intermediate of Formula (I-B) to form a compound of Formula (IV):

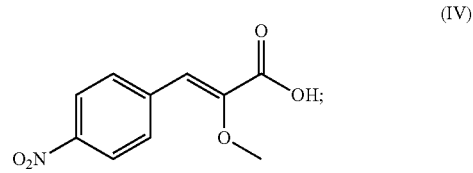 [SMILES: CO/C(=C\c1ccc([N+](=O)[O-])cc1)C(=O)O]

hydrogenating the compound of Formula (IV) to form a compound of Formula (V):

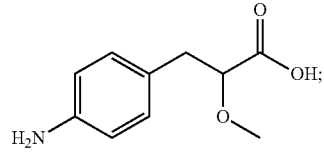

(V)

optionally resolving the compound of Formula (V) to form a substantially optically pure compound of Formula (VI):

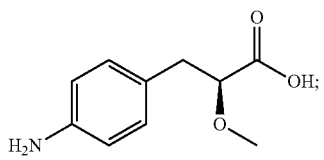

(VI)

and acylating the compound of Formula (VI) to form the compound of Formula (VII).

Reacting a compound of Formula (I) with an activating agent may comprise reacting in the presence of a base and a solvent. In some embodiments, the solvent is selected from the group consisting of toluene, dichloromethane, tetrahydrofuran, diethyl ether, 2-methyltetrahydrofuran, and acetonitrile, for example, the solvent may be toluene. The base may be an amine base, for example, selected from the group consisting of triethylamine, N,N-diisopropylethylamine, and pyridine. For example, the amine base may be triethylamine.

The compound of Formula (I) can be an isolated solid prior to this step or can be dissolved in an appropriate solvent, for example, a solvent used in making or working up the compound of Formula (I). For example, the compound of Formula (I) can be unisolated and dissolved in an organic solvent, e.g., toluene, prior to this step.

Contemplated activating agent includes a sulfonylating agent, or a halogenating agent. For example, the activating agent may be selected from the group consisting of a methanesulfonyl chloride, p-toluenesulfonyl chloride, p-bromobenzenesulfonyl chloride, phenyl triflimide, triflic anhydride, and nonafluorobutanesulfonic anhydride. In some embodiments, the activating agent is methanesulfonyl chloride.

In some embodiments, the leaving group is selected from the group consisting of —OSO$_2$-aryl, —OSO$_2$—C$_{1-4}$alkyl, chloro, bromo, and iodo; wherein C$_{1-4}$alkyl and aryl may be optionally substituted with one or more substituents each independently selected, for each occurrence, from the group consisting of fluoro, bromo, and —CH$_3$. For example, the leaving group may be —OSO$_2$-phenyl or —OSO$_2$—C$_{1-4}$alkyl.

In some embodiments, the leaving group is selected from the group consisting of: —OSO$_2$Me,

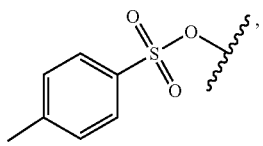 [SMILES: *OS(=O)(=O)c1ccc(C)cc1]

—OSO$_2$CF$_3$,

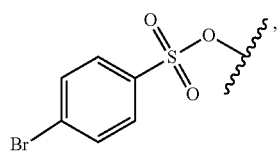

and —OSO$_2$CF$_2$CF$_2$CF$_2$CF$_3$, e.g., the leaving group may be —OSO$_2$Me.

Contemplated alcohol solvents may include at least one of methanol, ethanol, isopropanol, and butanol. For example, the alcohol solvent may include methanol.

In some embodiments, the base solution, comprises at least one of: sodium hydroxide, lithium hydroxide, and potassium hydroxide. For example, a base solution may include sodium hydroxide, for example, 30% sodium hydroxide.

In some embodiments, hydrolyzing the intermediate of Formula (I-B) to form a compound of Formula (IV) comprises: contacting the intermediate of Formula (I-B) with an alkali hydroxide (e.g., sodium hydroxide) and water; and neutralizing to form the compound of Formula (IV). Neutralizing can include acidifying to a pH of less than or equal to 3 by adding an acid, for example, phosphoric acid or hydrochloric acid, or a mixture thereof.

In some embodiments, hydrogenating the compound of Formula (IV) to form a compound of Formula (V) comprises contacting the compound of Formula (IV) with hydrogen and a catalyst, for example, a catalyst selected from the group consisting of PtO$_2$, Pd(OH)$_2$/C, Pt/C, 10% Pd/C, and 5% Pd/C, e.g., 5% Pd/C catalyst. Hydrogenating may be performed at a reaction temperature which is maintained between about 60-80° C. and at a pressure between about 3 to 5 atm, about 3.5 to 4.5 atm, or about 4.0 to 4.5 atm. For example, hydrogenating may be performed in the presence of one or more hydrogenation solvents selected from the group consisting of an aqueous ammonia solution, methanol, ethanol, isopropanol, N,N-dimethylformamide, tetrahydrofuran and ethyl acetate, e.g., an aqueous ammonia solution, methanol, or N,N-dimethylformamide. In some embodiments the hydrogenation solvent is methanol or a mixture of methanol and ammonia, e.g., a 30% ammonia aqueous solution.

Following hydrogenation, the compound of Formula (V) may optionally be isolated by contacting the solution with an acid, for example, acetic acid or hydrochloric acid, or a mixture thereof.

Resolving the compound of Formula (V) to form a substantially optically pure compound of Formula (VI) may include:
  a) resolving a compound of Formula (V) in the presence of a chiral acid thereby forming a chiral salt of the compound of Formula (VI); and
  b) neutralizing the chiral salt of the compound of Formula (VI) thereby forming the compound of Formula (VI).

In some embodiments, the chiral acid is selected from the group consisting of (S)-(+)-camphor-10-sulfonic acid, (2R, 3R)-(+)-tartaric acid, (S)-(−)-malic acid, (1S)-(+)-3-bromo-camphor-10-sulfonic acid, (S)-1-phenylethane sulphonic acid, dibenzoyl-L-tartaric acid, glutamic acid, (1R, 3S)-camphoric acid, (1S)-camphanic acid and (R)-(−)-mandelic acid and all other chiral acids that can lead to resolution of racemic mixture or an enantiomer thereof, e.g., (S)-(+)-camphor-10-sulfonic acid.

In some embodiments, the chiral salt of the compound of Formula (VI) is:

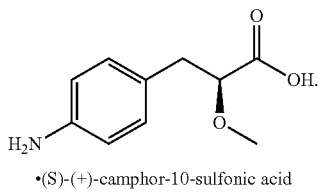

•(S)-(+)-camphor-10-sulfonic acid

In various embodiments, resolving may further comprise adding a primer and maintaining a temperature between 30-35° C. while stirring, and/or may occur in the presence of acetone and water. In some embodiments, resolving may further comprise maintaining a temperature between 55-60° C. (e.g., 58° C.) while stirring, and/or may occur in the presence of acetone and water.

A primer may be a substantially optically pure chiral acid salt of the compound of Formula (VI). In some embodiments, the chiral acid is (S)-(+)-camphor-10-sulfonic acid.

For example, the primer may be represented by:

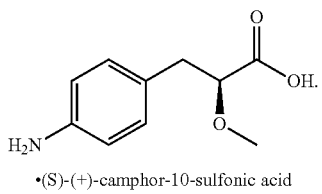

•(S)-(+)-camphor-10-sulfonic acid

At the end of resolving, if specifications are not met, reprocessing can occur where the solution maintained at the resolving temperature while stirring for a longer time.

Neutralizing may include contacting the chiral salt of the compound of Formula (VI), with (i) an aqueous base (e.g., ammonium hydroxide); and then (ii) acidifying the solution by adding an acid (e.g., acetic acid). Neutralizing may occur in the presence of one or more solvents, e.g., in the presence of water and ethyl acetate.

Acylating may include contacting the compound of Formula (VI) with an acylating agent (e.g., acetic anhydride) in the presence of an organic solvent selected from the group consisting of ethyl acetate, tetrahydrofuran, diethyl ether, dichloromethane, and toluene, e.g., ethyl acetate. Such acylating may occur at a temperature between 60 to 70° C., for example, between 65 to 70° C. Acylating may further comprise dissolving the compound isolated from the previous step in one or more solvents, e.g., water and/or ethyl acetate, to prepare a solution and contacting the solution with an acylating agent, e.g., acetic acid. Such step may occur at a temperature between 60 to 70° C., for example, at a temperature between 65 to 70° C.

In some embodiments, after optionally resolving the compound of Formula (V) to form a substantially optically pure compound of Formula (VI), a mother liquor derived from resolution step may still contain the desired enantiomer (as a salt of the resolving agent) together with the undesired one. In these embodiments, resolving may optionally further comprise:

a) recovering the mixture of enantiomers (as chiral salts of the resolving agent) from the mother liquor, neutralizing the chiral salts to form a compound of Formula (V), and resolving the compound of Formula (V) providing additional substantially optically pure compound of Formula (VI), thereby increasing the total process yield; or b) distilling part of the mother liquor and precipitating the desired enantiomer as a salt of the chiral resolving agent from the mother liquor, thereby increasing the total process yield.

Also contemplated herein is a process of racemizing the undesired enantiomer or chiral salt thereof in the presence of a base and resolving the resulting mixture of (R), and (S) enantiomers using a resolution process contemplated herein to form the desired enantiomer.

Contemplated bases include those selected from the group consisting of hydroxides, alkoxides (e.g., methoxide), amides (e.g., lithium diisopropylamide), hydrides (e.g., NaH), organolithiums, and Grignard reagents. For bases that require a counterion, exemplary counterions contemplated herein may include alkali metals or alkaline earth metals e.g., lithium, sodium, potassium, or calcium; or organic counterions e.g., tetraalkyl ammoniums.

In some embodiments, the compound of Formula (VII) can be produced on a multi-kilogram scale, for example, at least about 8 to 11 kg, about 13 to 15 kg, or about 130 to 150 kg is obtained. In some embodiments, at least about 130 kg of the compound of Formula (VII) is obtained.

In some embodiments, the substantially optically pure compound of Formula (VII) is at least 98% of the desired enantiomer:

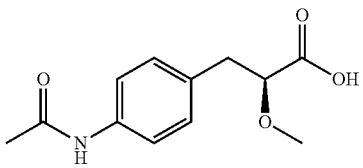 [SMILES: CO[C@@H](Cc1ccc(NC(C)=O)cc1)C(=O)O]

(expressed as a percentage of both enantiomers). In some embodiments, the content of (S)-(−)-3-(4-aminophenyl)-2-methoxypropionic acid may not, for example, be more than 0.15% by HPLC.

In an alternative embodiment a disclosed preparation of a substantially optically pure compound of Formula (VII) comprises acylating racemic compound (V) yielding a racemic mixture of 3-(4-acetamidophenyl)-2-methoxypropionic acid, and resolving the racemic 3-(4-cetamidophenyl)-2-methoxypropionic acid to provide substantially enantiomerically pure compound of Formula (VII). For example, forming substantially optically pure compound of Formula (VII) may comprise:

a) resolving a racemic mixture of 3-(4-acetamidophenyl)-2-methoxypropionic acid in the presence of a chiral base thereby forming a chiral salt of the compound; and b) neutralizing the chiral salt of the compound thereby forming the compound of Formula (VII).

In some embodiments, the chiral base is selected from the group consisting of e.g., enantiomerically pure 1-amino-2- propanol, brucine, dehydroabietylamine, N,α-dimethylbenzylamine, N,N-dimethyl-1-phenylethylamine, ephedrine, α-methylbenzylamine, 1-(2-naphthyl)ethylamine, quinidine, quinine, strychnine, valine and all other chiral bases that can lead to resolution of racemic mixture. For example, a chiral salt of the compound can be represented by:

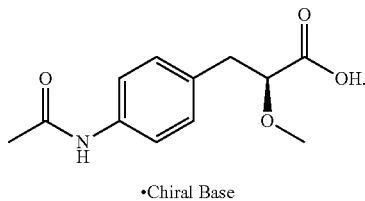 [SMILES: CO[C@@H](Cc1ccc(NC(C)=O)cc1)C(=O)O]

·Chiral Base

In certain embodiments, the present disclosure provides a process for preparing a compound of Formula (I):

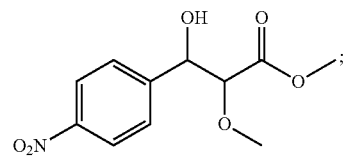

(I)

the process comprising, providing a mixture of a compound of Formula (II):

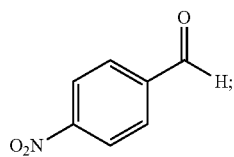

(II)

and a compound of Formula (III):

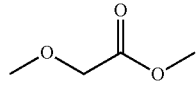

(III)

and contacting the mixture with a base (e.g., in a solvent such as tetrahydrofuran); thereby forming a compound of Formula (I).

Contacting may be performed at a temperature less than or equal to 10° C., e.g., may comprise stirring for about 5 minutes and/or is performed at a reaction temperature which is maintained between −10 to 10° C., for example, between −5 to 0° C. The base may be an alkali metal alkoxide, e.g., selected from the group consisting of sodium methoxide, lithium methoxide, and potassium methoxide, for example, sodium methoxide.

In some embodiments, provided herein is a compound represented by:

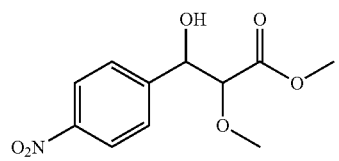

(I)

or a pharmaceutically acceptable salt or stereoisomer thereof.

In some embodiments, a compound of Formula (I) may exist as a mixture of stereoisomers. Contemplated stereoisomers of Formula (I) include e.g., compounds of Formula (a), Formula (b), Formula (c), or Formula (d):

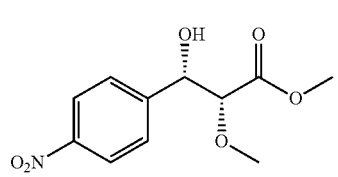

(a)

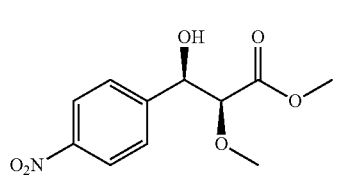

(b)

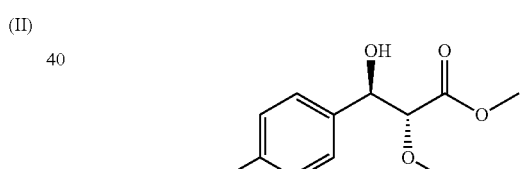

(c)

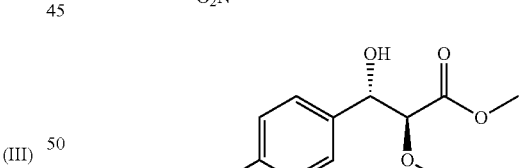

(d)

Also provided herein in part is a process for preparing a substantially optically pure compound of Formula (VI):

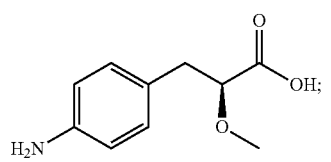

(VI)

the process comprising: reacting a compound of Formula (I):

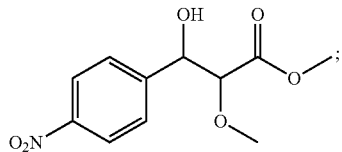

with an activating agent, in the optional presence of a base, to form an intermediate of Formula (I-A):

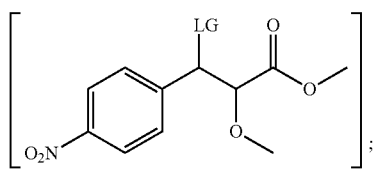

wherein LG is a leaving group;
treating the intermediate of Formula (I-A) with a base solution in the presence of an alcohol solvent, to eliminate the leaving group and thereby forming an intermediate of Formula (I-B):

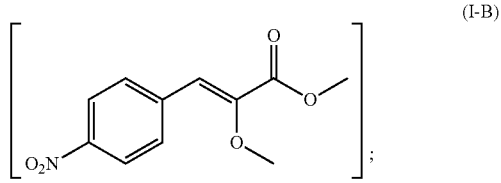

hydrolyzing the intermediate of Formula (I-B) to form a compound of Formula (IV):

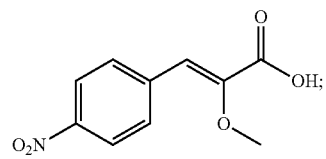

hydrogenating the compound of Formula (IV) to form a compound of Formula (V):

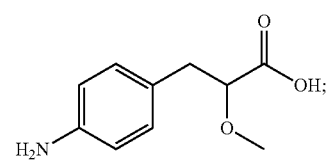

resolving the compound of Formula (V) to form a substantially optically pure compound of Formula (VI), wherein the process and variables are as defined herein.

Procedures for making compounds described herein are provided below with reference to Schemes 1-21. In the reactions described below, it may be necessary to protect reactive functional groups (such as hydroxyl, amino, or carboxyl groups) to avoid their unwanted participation in the reactions. The incorporation of such groups, and the methods required to introduce and remove them are known to those skilled in the art (for example, see Greene, Wuts, Protective Groups in Organic Synthesis. 4th Ed. (2007)). The deprotection step may be the final step in the synthesis such that the removal of protecting groups affords compounds of Formula I, as disclosed herein. Starting materials used in the following schemes can be purchased or prepared by methods described in the chemical literature, or by adaptations thereof, using methods known by those skilled in the art. The order in which the steps are performed can vary depending on the groups introduced and the reagents used, but would be apparent to those skilled in the art.

EXAMPLES

The procedures disclosed herein can be conducted in a number of ways based on the teachings contained herein and synthetic procedures known in the art. In the description of the synthetic methods described below, it is to be understood that all proposed reaction conditions, including choice of solvent, reaction atmosphere, reaction temperature, duration of the experiment and workup procedures, can be chosen to be the conditions standard for that reaction, unless otherwise indicated. It is understood by one skilled in the art of organic synthesis that the functionality present on various portions of the molecule should be compatible with the reagents and reactions proposed. Substituents not compatible with the reaction conditions will be apparent to one skilled in the art, and alternate methods are therefore indicated. The starting materials for the examples are either commercially available or are readily prepared by standard methods from known materials.

At least some of the compounds identified as intermediates e.g., as part of a synthetic scheme disclosed herein are contemplated as compounds of the disclosure Abbreviations:
General:
APCI atmospheric pressure chemical ionization
DSC differential scanning calorimetry
EA elemental analysis
ESI electrospray ionization
GC gas chromatography
HPLC high-performance liquid chromatography
ICP-AES inductively coupled plasma atomic emission spectroscopy
LC liquid chromatography
MHz megahertz
MS mass spectrometry
NMR nuclear magnetic resonance
TLC thin layer chromatography
Me methyl
Ph phenyl
Et ethyl
Solvents and Reagents
CSA camphorsulfonic acid
DMF N,N-dimethylformamide
EtOAc ethyl acetate
Mesyl methanesulfonyl
NaOMe sodium methoxide
THF tetrahydrofuran General Experimental:

$^1$H NMR spectra were recorded using a Varian Gemini 200 NMR-spectrometer operating at 200 MHz or 600 MHz. Chemical shifts for protons were reported as parts per million in δ scale using solvent residual peak (DMSO-$d_6$: 2.50 ppm) as an internal standard. Data are represented as follows: chemical shift (δ), multiplicity (s=singlet, d=doublet, t=triplet, q=quartet, qn=quintuplet, sx=sextet, sp=septuplet, m=multiplet, br=broad, dd=doublet of doublets, dt=doublet of triplets, qd=quartet of doublets, dquin=doublet of quintets), coupling constant (J, Hz) and integration (#H).

$^{13}$C NMR were recorded dissolving the sample in DMSO-$d_6$ operating at 600 MHz. Full decoupled spectra were acquired.

Mass spectra were recorded on an Thermo-Finnigan LCQ-Advantage mass-spectrometer or MS Thermo LCQ-fleet. The LC/MS data were obtained using positive/negative mode switching or using a negative mode polarity with acquisition parameters optimized in negative polarity on signal 236 m/z corresponding to the quasi-molecular ion [M−H]$^−$ of the sample.

The elemental analysis (CHN) was carried out by Carlo Erba EA1108 equipment under the following conditions: sample weight: 0.5-2 mg; furnace temperature: 1010° C.; column temperature: 80° C.; gas: He; flow: 100 mL/min. The elemental analysis (Oxygen) was carried out by Carlo Erba EA1108 equipment under the following conditions: sample weight: 0.5-2 mg; furnace temperature: 1010° C.; column temperature: 60° C.; gas: He; flow: 100 mL/min.

FT-IR spectroscopy FT-IR/ATR was performed on the sample as such with a Perkin Elmer spectrometer model Spectrum Two instrument equipped with a diamond probe. The spectrum was collected in the frequency range of 450-4000 cm$^{-1}$.

UV-visible spectrum was recorded with a spectrophotometer Shimadzu UV 2600 working under the following conditions: cuvette: quartz 1 cm; range: 200-600 nm; scan speed: medium; scan step: 1 nm; slit width: 1.0 nm; Reference solution: methanol; sample solution: 1 mg of sample was dissolved in 100 mL of methanol.

DSC was performed using a Mettler-Toledo TGA-DSC1 instrument working in the following conditions (pan: aluminum (open); heating rate: 10° C./min; gas: Nitrogen; flow: 30 mL/min).

Specific optical rotation was determined as follows. In a 50 mL volumetric flask accurately weigh 0.5 g of the sample, dissolve and dilute to volume with methanol (concentration: 10 mg/mL corresponding to 1% w/v). Determine the rotation angle of the obtained solution, using a polarimeter tube having an optical length corresponding to 1 dm.

Calculate the specific optical rotation $[α]_D^{20}$ referred to the dried substance with the following formula: (α×50×100)/(W×(100−m)), where α=read rotation angle; W=sample weight (g); and m=sample water content (%).

Chiral purity (HPLC) was determined as follows.

| Apparatus and operative conditions | |
|---|---|
| Chromatograph | HPLC Waters equipped with pump, injector, UV-Vis spectrophotometer and Empower integration system (or equivalent) |
| Column | DaicelChiralpak WH, 10 μm 250 mm × 4.6 mm I.D. (Daicel Chemical Industries DAIC25625) |
| Mobile phase A | dissolve 62.5 mg of CuSO$_4$·5H$_2$O in 1000 mL of water |

-continued

| Apparatus and operative conditions | |
|---|---|
| Mobile phase | Prepare a 90:10 (v/v) mixture of Mobile phase A/acetonitrile |
| Flow rate | 1.0 mL/min |
| Column temperature | 45° C. |
| Injected volume | 20 μl |
| Wavelength | 258 nm |

Preparation of the Solutions

Sample solution: in a 10 mL volumetric flask accurately weigh 10 mg of the sample, then dissolve and dilute to volume with mobile phase (concentration: 1000 μg/mL).

Reference solution: in a 100 mL volumetric flask accurately weight 10 mg of (R,S)-3-(4-Acetamidophenyl)-2-methoxypropionic acid standard, then dissolve and dilute to volume with mobile phase.

System suitability test (SST) solution: in a 10 mL volumetric flask accurately weight 10 mg of (S)-(−)-3-(4-Acetamidophenyl)-2-methoxypropionic acid standard, add 2 mL of reference solution, then dissolve and dilute to volume with mobile phase (final concentration of the dextrorotatory enantiomer: 10 μg/mL corresponding to 1% with reference to the sample solution, corresponding to 99% of chiral purity of (S)-(−)-3-(4-Acetamidophenyl)-2-methoxypropionic acid).

System Suitability Test and Procedure

Inject 20 μl of the sample solution and of SST solution in the chromatograph and record the chromatogram.

The elution order of the main peaks is as follows. (R)-(+)-3-(4-Acetamidophenyl)-2-methoxypropionic acid (dextrorotatory enantiomer): RRT=0.9; and (S)-(−)-3-(4-Acetamidophenyl)-2-methoxypropionic acid (levorotatory enantiomer): RRT=1.0.

The chromatographic system can be used for the test if the h/v ratio is not less than 1.5, where h is the distance between the top of the peak due to the dextrorotatory enantiomer and the baseline, v is the distance between the lowest point of the valley defined between dextrorotatory enantiomer peak and levorotatory enantiomer one and the baseline.

The chiral purity % is calculated from the following expression: $(A_l×100)/(A_l+A_d)$, where $A_l$=(S)-(−)-3-(4-Acetamidophenyl)-2-methoxypropionic acid peak area in the sample solution (levorotatory enantiomer) and $A_d$=(R)-(+)-3-(4-Acetamidophenyl)-2-methoxypropionic acid peak area in the sample solution (dextrorotatory enantiomer).

The above method may be used to determine optical purity or enantiomeric purity of a compound as referenced herein.

Example 1: Preparation of methyl 3-hydroxy-2-methoxy-3-(4-nitrophenyl)propionate (I)

Scheme 1.

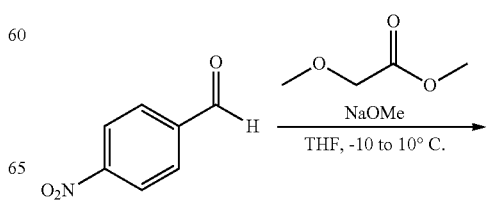

-continued

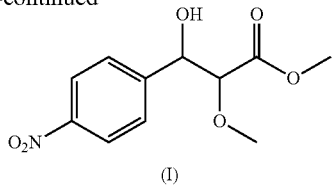

(I)

TABLE 1

Batch formula at production scale (synthesis of compound (I))

| Material | Factor* | Amount (kg) |
| --- | --- | --- |
| sodium methoxide | 0.6 | 30.0 |
| THF | 1.5 | 75 |
| 4-nitrobenzaldehyde | 1.0 | 50 |
| methyl methoxyacetate | 1.1 | 55 |
| THF | 2.0 | 100 |
| THF | 0.5 | 25.0 |
| cold toluene | 2.0 | 100 |
| glacial acetic acid | 1.0 | 50 |
| deionized water | 3.0 | 150 |
| deionized water | 2.0 | 100 |
| sodium chloride | 0.2 | 10 |
| deionized water | 2.0 | 100 |
| sodium chloride | 0.2 | 10 |
| toluene | 1.0 | 50 |
| toluene | 1.5 | 75 |
| cold toluene | 0.5 | 25 |

*factor is referenced to the amount of 4-nitrobenzaldehyde used

Preparation of 4-nitrobenzaldehyde in methyl methoxyacetate and tetrahydrofuran Suspension:

A stainless steel reactor was charged with 4-nitrobenzaldehyde (50 kg), methyl methoxyacetate (55 kg) and tetrahydrofuran (100 kg) and cooled to −5 to +5° C. while stirring.

Preparation of methyl 3-hydroxy-2-methoxy-3-(4-nitrophenyl)propionate (I):

A stainless steel reactor was flushed with nitrogen (2×), and charged with sodium methoxide (30.0 kg) and tetrahydrofuran (75 kg) while flushing with nitrogen. The reactor was then flushed with nitrogen for 1 min and the sodium methoxide solution cooled to −10 to −5° C., while stirring. The cooled solution was then treated with the previously prepared suspension of 4-nitrobenzaldehyde in methyl methoxyacetate and tetrahydrofuran maintaining the temperature of the reaction mass below 10° C. After the addition was complete, the empty reactor was rinsed with tetrahydrofuran (25.0 kg) and poured into the reaction. The reaction was stirred at −10 to +10° C. for no more than 5 minutes. Maintaining the temperature at −10 to +10° C., cold toluene (100 kg, −10 to 0° C.) followed by glacial acetic acid (50 kg) were slowly added and the reaction stirred for 10 minutes at −10 to +10° C. Deionized water (150 kg) was added and the reaction mass stirred at 0 to 10° C. for at least 10 minutes, then at 20 to 30° C. for at least 10 minutes to ensure complete dissolution, after which time stirring was stopped and the phases allowed to separate. The aqueous phase was eliminated, and the separated organic phase was treated with aqueous sodium chloride solution (previously prepared by adding 10 kg of sodium chloride to 100 kg of deionized water). The mass was then heated to 50 to 60° C., while stirring for at least 10 minutes. Stirring was stopped and the phases allowed to separate. The aqueous phase was eliminated and the organic phase treated with sodium chloride (previously prepared by adding 10 kg of sodium chloride with 100 kg of deionized water). The mass was extracted once more using the same protocol. The separated organic phase was then distilled under vacuum, without exceeding 80° C. to remove THF. The reactor containing the hot residue was flushed with nitrogen then treated with toluene (50 kg), and the toluene distilled under vacuum, without exceeding 80° C. The resulting hot residue was flushed with nitrogen then treated with toluene (75 kg) and the mass stirred for at least 30 minutes at 30 to 45° C. to ensure good product precipitation. The mixture was then cooled to −10 to 0° C. and stirred at for at least 1 hour at that temperature. The resulting suspension was centrifuged portion-wise, washing with cold toluene (25 kg) to obtain wet methyl 3-hydroxy-2-methoxy-3-(4-nitrophenyl)propanoate (I) (84 kg), which was used directly.

Methyl 3-hydroxy-2-methoxy-3-(4-nitrophenyl)propanoate (I): IR: 3468, 1737, 1514, 1350, 1201, 1101 cm⁻; LCMS (−)APCI: m/z calculated for $C_{11}H_{13}NO_6$: 255, found: 254 (M−H); $^1$H NMR (200 MHz, DMSO-$d_6$): δ 8.16 (AA'BB' system, J=8.8 Hz, 2H), 7.62 (AA'BB' system, J=8.8 Hz, 2H), 5.97 (d, J=6.0 Hz, 1H), 5.05 (dd, J=6.0, 4.0 Hz, 1H), 4.10 (d, J=4.0 Hz, 1H), 3.60 (s, 3H), 3.20 (s, 3H); $^{13}$C NMR (150 MHz, DMSO-$d_6$): δ 170.2, 149.4, 146.7, 127.8, 122.9, 84.1, 72.7, 58.2, 51.6; UV-Vis (MeOH): $\lambda_{max}$ 202, 270; Anal. calcd for: ($C_{11}H_{13}NO_6$): C 51.97; H 5.16; N 5.42; O 37.52.

Example 2: Preparation of (S)-(−)-3-(4-Aminophenyl)-2-methoxypropionic acid (VI) and (S)-(−)-3-(4-Acetamidophenyl)-2-methoxypropionic acid (VII)

Scheme 2.

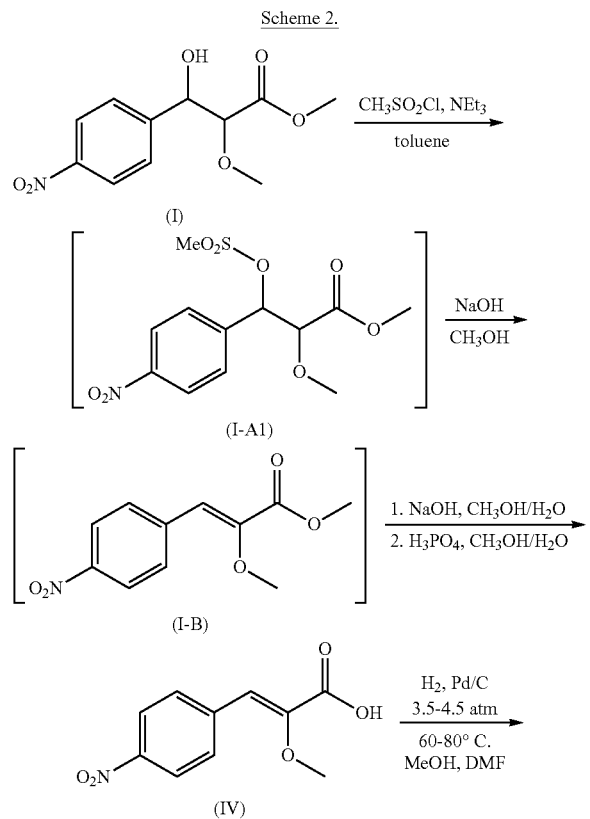

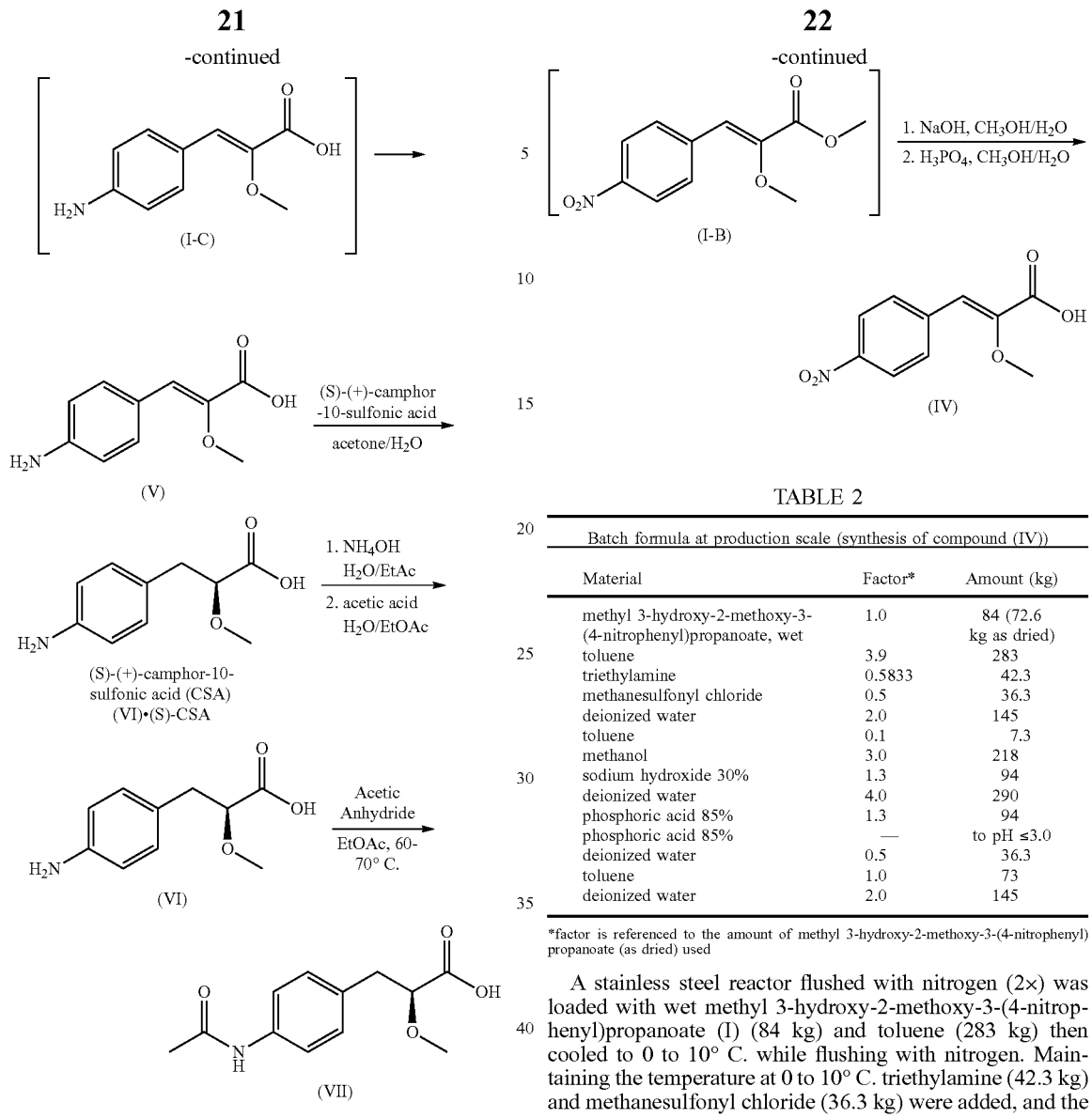

Preparation of 2-methoxy-3-(4-nitrophenyl)acrylic Acid (IV):

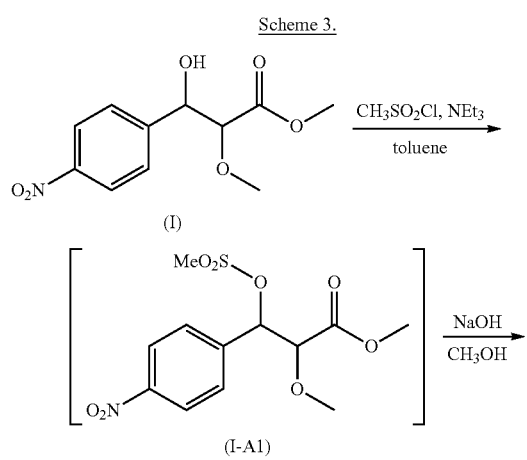

TABLE 2

Batch formula at production scale (synthesis of compound (IV))

| Material | Factor* | Amount (kg) |
|---|---|---|
| methyl 3-hydroxy-2-methoxy-3-(4-nitrophenyl)propanoate, wet | 1.0 | 84 (72.6 kg as dried) |
| toluene | 3.9 | 283 |
| triethylamine | 0.5833 | 42.3 |
| methanesulfonyl chloride | 0.5 | 36.3 |
| deionized water | 2.0 | 145 |
| toluene | 0.1 | 7.3 |
| methanol | 3.0 | 218 |
| sodium hydroxide 30% | 1.3 | 94 |
| deionized water | 4.0 | 290 |
| phosphoric acid 85% | 1.3 | 94 |
| phosphoric acid 85% | — | to pH ≤3.0 |
| deionized water | 0.5 | 36.3 |
| toluene | 1.0 | 73 |
| deionized water | 2.0 | 145 |

*factor is referenced to the amount of methyl 3-hydroxy-2-methoxy-3-(4-nitrophenyl)propanoate (as dried) used A stainless steel reactor flushed with nitrogen (2×) was loaded with wet methyl 3-hydroxy-2-methoxy-3-(4-nitrophenyl)propanoate (I) (84 kg) and toluene (283 kg) then cooled to 0 to 10° C. while flushing with nitrogen. Maintaining the temperature at 0 to 10° C. triethylamine (42.3 kg) and methanesulfonyl chloride (36.3 kg) were added, and the reaction stirred at 0 to 10° C. for 30 minutes. Deionized water (145 kg) was slowly added, and the resulting mass stirred at 50 to 60° C. for 10 minutes, after which time stirring was stopped and the phases were allowed to separate. The aqueous phase was eliminated and the organic phase filtered washing with toluene (7.3 kg). The toluene was removed by distillation under vacuum and without exceeding 60° C., to obtain an oily residue. The resulting residue was then treated with methanol (218 kg), transferred to another reactor, flushed with nitrogen, cooled to 20 to 30° C. and treated slowly with 30% sodium hydroxide (94 kg). The reaction was stirred at 20 to 30° C. for 2 hours. Deionized water (290 kg) was added, and the solution heated to 55 to 65° C. At this temperature, 85% phosphoric acid (94 Kg) was slowly added until a pH ≤3.0 was obtained. The resulting precipitated product was stirred at 55 to 65° C. for at least 30 minutes then cooled to 25 to 30° C., and stirred for at least 30 minutes. The mixture was centrifuged washing with deionized water (36.3 kg), toluene (73 kg), and deionized water (145 kg). The product was granulated and dried at 70 to 80° C. to deliver 2-methoxy-3-(4-nitrophenyl) acrylic acid (IV) (50.4 kg).

Methyl 2-methoxy-3-((methylsulfonyl)oxy)-3-(4-nitrophenyl)propanoate (I-A1) LCMS (+)ESI: m/z calculated for $C_{12}H_{15}NO_8S$: 333; found 356 (M+Na); $^1$H NMR (200 MHz, DMSO-d$_6$): δ 8.25 (AA'BB' system, J=8.5 Hz, 2H), 7.72 (AA'BB' system, J=8.5 Hz, 2H), 6.00 (d, J=4.0 Hz, 1H), 4.41 (d, J=4.0 Hz, 1H), 3.65 (s, 3H), 3.21 (s, 3H), 3.11 (s, 3H).

Methyl 2-methoxy-3-(4-nitrophenyl)acrylate (I-B): LCMS (−)APCI: m/z calculated for $C_{11}H_{11}NO_5$: 237; found 236 M−H); $^1$H NMR (200 MHz, DMSO-d$_6$): δ 8.20 (AA'BB' system, J=8.8 Hz, 2H), 7.99 (AA'BB' system, J=8.8 Hz, 2H), 6.98 (s, 1H), 3.80 (s, 3H), 3.78 (s, 3H).

2-Methoxy-3-(4-nitrophenyl)acrylic acid (IV): LCMS (−)APCI: m/z calculated for $C_{10}H_9NO_5$: 223, found: 222 (M−H); $^1$H NMR (200 MHz, DMSO-d$_6$): δ 13.37 (s, 1H), 8.21 (AA'BB' system, J=9.1 Hz, 2H), 7.98 (AA'BB' system, J=9.1 Hz, 2H), 6.93 (s, 1H), 3.79 (s, 3H).

Preparation of 3-(4-aminophenyl)-2-methoxypropanoic Acid (V):

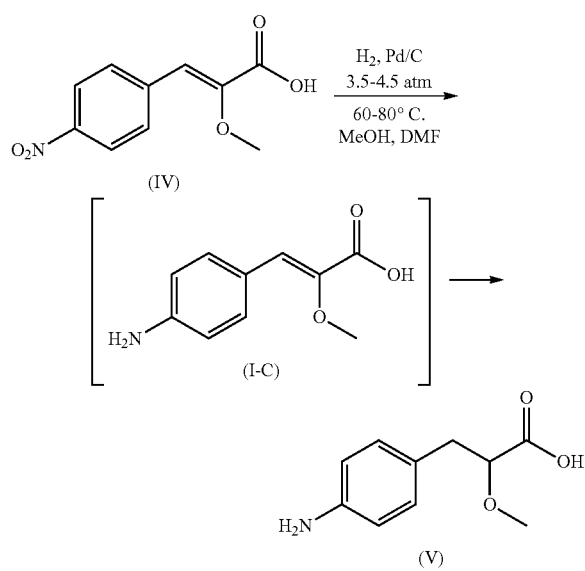

Scheme 4.

TABLE 3

Batch formula at production scale (synthesis of compound (V))

| Material | Factor* | Amount (kg) |
|---|---|---|
| 2-methoxy-3-(4-nitrophenyl)acrylic acid, dried | 1.0 | 50.4 |
| methanol | 5.0 | 252 |
| N,N-dimethylformamide | 0.3421 | 17.2 |
| palladium on carbon 5% (containing 50% water) | 0.1 | 7.7 |
| N,N-dimethylformamide | 0.0526 | 2.65 |
| N,N-dimethylformamide | 0.0526 | 2.65 |
| N,N-dimethylformamide | 0.0526 | 2.65 |
| ammonia (30%) | 0.4 | 20.2 |
| deionized water | 0.25 | 12.6 |
| deionized water | 0.5 | 25.2 |
| deionized water | 3.0 | 151 |
| acetic acid 80% | 0.5 | 25.2 |
| ethyl acetate | 1.0 | 50 |
| deionized water | 2.0 | 101 |
| ethyl acetate | 0.5 | 25.2 |

*factor is referenced to the amount of dried 2-methoxy-3-(4-nitrophenyl)acrylic acid used A suitable stainless steel reactor was loaded with N,N-dimethylformamide (17.2 kg), 5% palladium on carbon (7.7 kg) and N,N-dimethylformamide (2×2.65 kg) and the suspension stirred thoroughly.

A stainless steel reactor flushed with nitrogen (2×) charged with methanol (252 kg) was cooled to 0 to 10° C. and dry 2-methoxy-3-(4-nitrophenyl)acrylic acid (IV) (50.4 kg) was added. The resulting solution was flushed with nitrogen (2×) and treated with a previously prepared solution of 5% palladium on carbon in N,N-dimethylformamide, and the empty vessel was washed with N,N-dimethylformamide (2.65 kg). The reaction was flushed with nitrogen (2×), heated to 60 to 80° C. then charged with hydrogen until a pressure of 3.5 and 4.5 atm was obtained. The reaction was allowed to proceed, maintaining the pressure between 3.5 and 4.5 atm until hydrogen consumption ceased and the reaction was confirmed complete. The reactor was restored to atmospheric pressure and the reaction was cooled to 20 to 30° C., flushed with nitrogen (2×) and treated sequentially with 30% ammonia (20.2 kg) and deionized water (12.6 kg), stirring at 20 to 30° C. until complete dissolution occurred. The solution was filtered through sparkler filter washing with deionized water (25.2 kg). The reactor was flushed with nitrogen, and the solvents were removed by vacuum distillation, at a temperature not exceeding 70° C. The residue was treated with deionized water (151 kg), heated to 60 to 70° C. and the product precipitated by adding 80% acetic acid (25.2 kg). The mixture was stirred at 60 to 70° C. for at least 10 minutes then treated with ethyl acetate (50 kg), flushed with nitrogen and stirred at 60 to 70° C. for at least 15 minutes. The reaction mass was cooled to 10 to 20° C. and stirred for at least 30 minutes. The suspension was centrifuged portion-wise washing with deionized water (101 kg) and ethyl acetate (25.2 kg). The moist product was granulated, and dried at 60 to 70° C. to obtain 3-(4-aminophenyl)-2-methoxypropanoic acid (V) (~37.5 kg).

3-(4-Aminophenyl)-2-methoxyacrylic acid (I-C): LCMS (+)ESI: m/z calculated for $C_{10}H_{11}NO_3$: 193, found 194 (M+H); $^1$H NMR (200 MHz, DMSO-d$_6$): δ 12.00 (br s, 1H), 7.43 (AA'BB' system, J=8.4 Hz, 2H), 6.76 (s, 1H), 6.53 (AA'BB' system, J=8.4 Hz, 2H), 5.80 (br s, 2H), 3.61 (s, 3H).

3-(4-Aminophenyl)-2-methoxypropanoic acid (V): IR: 3044, 2950-2830, 2623-2064, 1618-1516, 1106 cm$^{-1}$; LCMS (+)ESI: m/z calculated for $C_{10}H_{13}NO_3$: 195, found 196 (M+H); $^1$H NMR (200 MHz, DMSO-d$_6$): δ 8.40-6.40 (br s, 3H), 6.83 (AA'BB' system, J=8.1 Hz, 2H), 6.41 (AA'BB' system, J=8.1 Hz, 2H), 3.77 (ABX system, J=7.5, 5.3 Hz, 1H), 3.19 (s, 3H), 2.74 (ABX system, J=13.9, 5.3 Hz, 1H), 2.65 (ABX system, J=13.9, 7.5 Hz, 1H). Anal. calcd for: ($C_{10}H_{13}NO_3$): C 61.40; H 6.81; N 7.11; O 24.91.

Preparation of (S)-(−)-3-(4-Aminophenyl)-2-methoxypropionic acid S-(+)-camphor-10-sulfonic acid Salt:

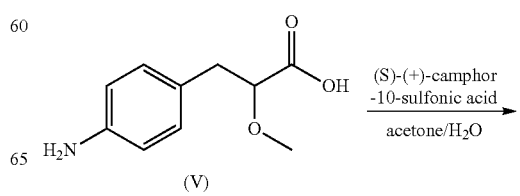

Scheme 5.

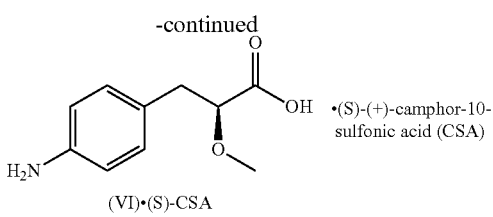

(VI)•(S)-CSA

TABLE 4

Batch formula at production scale (synthesis of compound (VI)•(S)-CSA)

| Material | Factor* | Amount (kg) |
| --- | --- | --- |
| 3-(4-aminophenyl)-2-methoxypropanoic acid | 1.0 | 37.5 |
| acetone | 3.0 | 113 |
| deionized water | 0.4 | 15.0 |
| (S)-(+)-10-camphor-sulfonic acid | 1.2321 | 46.2 |
| acetone | 2.0 | 75 |
| (S)-(−)-3-(4-Aminophenyl)-2-methoxypropionic acid S-(+)-camphor-10-sulfonic acid salt, dried (primer) | 0.01 | 0.38 |
| acetone | 2.0 | 75 |

*factor is referenced to the amount of 3-(4-aminophenyl)-2-methoxypropanoic acid (dried) used A stainless steel reactor was loaded with 3-(4-aminophenyl)-2-methoxypropanoic acid (V) (37.5 kg), and acetone (113 kg) while flushing with nitrogen. Deionized water (15.0 kg) and (S)-(+)-camphor-10-sulfonic acid (46.2 kg) were added and the reactor flushed with nitrogen. The reaction was heated to 45 to 55° C. until dissolution was complete. Acetone (75 kg) was added and the solution cooled to 30 to 35° C. and treated with primer (S)-(−)-3-(4-aminophenyl)-2-methoxypropionic acid S-(+)-camphor-10-sulfonic acid salt (VI)•(S)-CSA (0.38 kg). The reaction was stirred at 30 to 35° C. for at least 3 hours until good precipitation occurred. The suspension was centrifuged portion-wise washing with acetone (75 kg). The centrifuged product (S)-(−)-3-(4-aminophenyl)-2-methoxypropionic acid S-(+)-camphor-10-sulfonic acid salt (VI)•(S)-CSA (41.7 kg) was used directly in the next step.

Preparation of (S)-(−)-3-(4-Aminophenyl)-2-methoxypropionic Acid (VI):

Scheme 6.

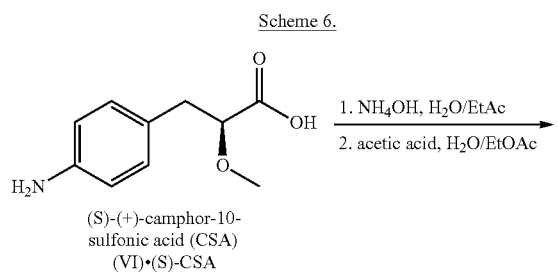

TABLE 5

Batch formula at production scale (synthesis of compound (VI))

| Material | Factor* | Amount (kg) |
| --- | --- | --- |
| (S)-(−)-3-(4-Aminophenyl)-2-methoxypropionic acid S-(+)-camphor-10-sulfonic acid salt, wet | 1.0 | 41.7 (35.0 kg as dried) |
| deionized water | 2.8 | 98 |
| deionized water | 0.2 | 7.0 |
| ethyl acetate | 1.0 | 35.0 |
| ammonia 30% | 0.1792 | 6.3 |
| acetic acid 80% | 0.125 | 4.38 |
| deionized water | 0.5 | 17.5 |
| ethyl acetate | 0.5 | 17.5 |
| deionized water | 0.5 | 17.5 |

*factor is referenced to the amount of (S)-(−)-3-(4-aminophenyl)-2-methoxypropionic acid S-(+)-camphor-10-sulfonic acid salt used (as dried).

Preparation of (S)-(−)-3-(4-Aminophenyl)-2-methoxypropionic acid (VI):

A stainless steel reactor was charged with deionized water (98 kg) and wet ((S)-(−)-3-(4-aminophenyl)-2-methoxypropionic acid S-(+)-camphor-10-sulfonic acid salt (VI)•(S)-CSA (41.7 kg), flushed with nitrogen and heated for at least 10 minutes at 20 to 30° C. until complete dissolution occurs. The solution was filtered washing with deionized water (7.0 kg), then ethyl acetate (35.0 kg). The resulting solution was flushed with nitrogen, heated to 50 to 60° C. and 30% ammonia (6.3 kg) was added to precipitate the product. The resulting mixture was stirred for at least 5 minutes at 50-60° C. then 80% acetic acid (4.38 kg) was added through a filter and the reaction flushed with nitrogen and stirred at 50 to 60° C. for at least 30 minutes then cooled down to 10-20° C. and stirred for at least 1 hour. The reaction was centrifuged portion-wise and washed with deionized water (17.5 kg), ethyl acetate (17.5 kg) and deionized water (17.5 kg), and dried at 50-60° C. to deliver (S)-(−)-3-(4-aminophenyl)-2-methoxypropionic acid (VI) (9.6 kg, 27%), which was used directly in the next step.

(S)-(−)-3-(4-Aminophenyl)-2-methoxypropionic acid (VI): $[\alpha]_D^{20}$ −30 to −26 (1% w/v $H_2O/CH_3OH$ (1:1 v/v)); IR: 2931, 2891, 2826, 2625, 2136, 1587, 1548, 1512, 1106, 1092 cm$^{-1}$; LCMS (+) ESI: m/z calculated for $C_{10}H_{13}NO_3$: 195, found 196 (M+H); $^1$H NMR (200 MHz, DMSO-$d_6$): δ 9.0-6.0 (br s, 3H), 6.83 (AA'BB' system, J=8.1 Hz, 2H), 6.43 (AA'BB' system, J=8.1 Hz, 2H), 3.76 (ABX system, J=7.5, 5.3 Hz, 1H), 3.19 (s, 3H), 2.75 (ABX system, J=13.9, 5.3 Hz, 1H), 2.65 (ABX system, J=13.9, 7.5 Hz, 1H). Anal. calcd for: ($C_{10}H_{13}NO_3$): C, 61.45; H, 6.79; N 7.12; O 24.65.

Preparation of (S)-(−)-3-(4-Acetamidophenyl)-2-methoxypropionic acid (VII):

Scheme 7.

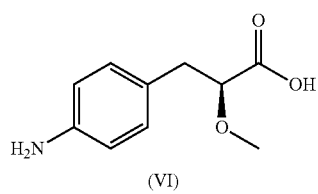

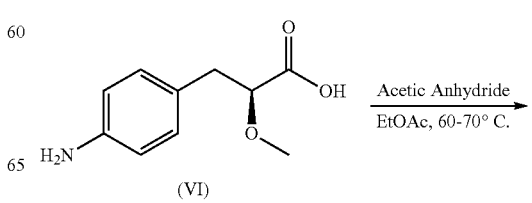

-continued

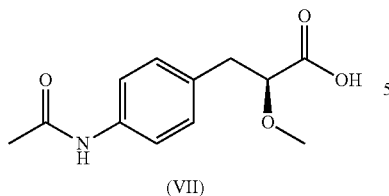

(VII)

TABLE 6

Batch formula at production scale (synthesis of compound (VII))

| Material | Factor* | Amount (kg) |
|---|---|---|
| (S)-(−)-3-(4-Aminophenyl)-2-methoxypropionic acid | 1.0 | 9.6 |
| ethyl acetate | 1.5 | 14.4 |
| acetic anhydride | 0.5833 | 5.6 |
| deionized water | 0.05 | 0.5 |
| ethyl acetate | 0.5 | 4.80 |
| deionized water | 1.5 | 14.4 |

*factor is referenced to the amount of (S)-(−)-3-(4-Aminophenyl)-2-methoxypropionic acid used A stainless steel reactor was charged with dry (S)-3-(4-aminophenyl)-2-methoxypropanoic acid (VI) (9.6 kg) and ethyl acetate (14.4 kg) at 0 to 10° C., while flushing with nitrogen. The reaction mass was heated to 60 to 70° C. and acetic anhydride (5.6 kg) was added through a cartridge filter over about 30 minutes. The reaction was stirred at 60 to 70° C. for 1 hour, then treated with deionized water (0.5 kg) and stirred at 60 to 70° C. for at least 15 minutes during which time a precipitate formed. The mixture was cooled to 10 to 20° C. and stirred for at least 30 minutes, then centrifuged and the resulting solid washed with ethyl acetate (4.80 kg), and deionized water (14.4 kg). The resulting product was dried at 60 to 70° C. for 13-16 hours, and milled to obtain (S)-3-(4-acetamidophenyl)-2-methoxypropanoic acid (VII) (10.3 kg).

(S)-(−)-3-(4-Acetamidophenyl)-2-methoxypropionic acid: (VII): $[\alpha]_D^{20}$ −26 to −19 (1% w/v $H_2O/CH_3OH$ (1:1 v/v)); IR: 3322, 3089, 2930, 2827, 2714, 2490, 1722, 1637, 1601, 1551, 1516, 1231, 1207, 1120, 1110 $cm^{-1}$; LCMS (+)ESI: m/z calculated for $C_{12}H_{15}NO_4$: 237, found 238 (M+H); $^1$H NMR (200 MHz, DMSO-$d_6$): δ 12.96 (s, 1H), 9.84 (s, 1H), 7.43 (AA'BB' system, J=8.5 Hz, 2H), 7.10 (AA'BB' system, J=8.5 Hz, 2H), 3.86 (ABX system, J=7.6, 5.2 Hz, 1H), 3.00 (s, 3H), 2.95-2.70 (ABX system, J=13.9, 7.6, 5.2 Hz, 2H), 2.00 (s, 3H).

TABLE 7

(S)-3-(4-acetamidophenyl)-2-methoxypropanoic acid (VII) specifications as prepared by Scheme 7

| | |
|---|---|
| (S)-(+)-camphor-10-sulfonic acid | No more than 0.1% (HPLC) |
| (S)-3-(4-aminophenyl)-2-methoxypropanoic acid | No more than 0.15% (HPLC) |
| Other impurity | No more than 0.1% (HPLC) |
| Palladium | No more than 10 ppm (ICP-AES) |
| Chiral purity | Not less than 98% (HPLC) |
| Acetic acid | No more than 5000 ppm (GC) |
| Residual solvents (ethyl acetate) | No more than 5000 ppm (GC) |

Example 3: Preparation of methyl 3-hydroxy-2-methoxy-3-(4-nitrophenyl)propionate (I)

Scheme 8.

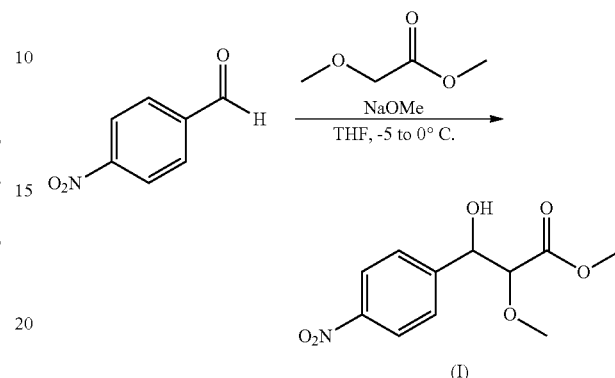

TABLE 8

Batch formula at production scale (synthesis of compound (I))

| Material | Factor* | Amount (kg) |
|---|---|---|
| sodium methoxide | 0.6 | 28.5 |
| THF | 2.5 | 119 |
| 4-nitrobenzaldehyde | 1.0 | 47.5 |
| methyl | 1.1 | 52 |
| THF | 1.0 | 47.5 |
| THF | 0.5 | 23.8 |
| cold toluene | 2.0 | 95 |
| glacial acetic acid | 0.75 | 36 |
| deionized water | 3.0 | 143 |
| deionized water | 1.0 | 48 |
| sodium chloride | 0.1 | 4.75 |
| toluene | 1.0 | 47.5 |
| toluene | 4.65 | 221 |

*factor is referenced to the amount of 4-nitrobenzaldehyde used

Preparation of 4-nitrobenzaldehyde in methyl methoxyacetate and tetrahydrofuran Suspension:

A stainless steel reactor was charged with 4-nitrobenzaldehyde (47.5 kg), methyl methoxyacetate (52 kg) and tetrahydrofuran (47.5 kg) and cooled to −10 to −5° C. while stirring.

Preparation of methyl 3-hydroxy-2-methoxy-3-(4-nitrophenyl)propionate (I):

A stainless steel reactor was flushed with nitrogen (2×), and charged with sodium methoxide (28.5 kg) and tetrahydrofuran (119 kg) while flushing with nitrogen. The reactor was then flushed with nitrogen for 1 min and the sodium methoxide solution was cooled to −10 to −7° C., while stirring. The cooled solution was then treated with the previously prepared suspension of 4-nitrobenzaldehyde in methyl methoxyacetate and tetrahydrofuran while maintaining the temperature of the reaction mass below 0° C. After the addition was complete, the empty reactor was rinsed with tetrahydrofuran (23.8 kg) and poured into the reaction. The reaction was stirred at −5 to 0° C. for no more than 5 minutes. Maintaining the temperature at −10 to 0° C., cold toluene (95 kg, −10 to 0° C.) was quickly added and then, after, glacial acetic acid (36 kg) was quickly added and the reaction was stirred for 10 minutes at −10 to +10° C. Deionized water (143 kg) was added and the reaction mass was stirred at 0 to 10° C. for at least 10 minutes, then at 25 to 30° C. for at least 10 minutes to ensure complete dissolution, after which time stirring was stopped and the phases were allowed to separate. The aqueous phase was eliminated, and the separated organic phase was treated with aqueous sodium chloride solution (previously prepared by adding 4.75 kg of sodium chloride to 48 kg of deionized water). The mass was then heated to 25 to 30° C., while stirring for at least 15 minutes. Stirring was stopped and the phases were allowed to separate. The aqueous phase was eliminated (64 kg). The separated organic phase was then distilled up to oily residue under vacuum, up to a temperature of 70 to 80° C. The reactor containing the hot residue was flushed with nitrogen then treated with toluene (47.5 kg), and the toluene was distilled under vacuum, up to a temperature of 70 to 80° C., obtaining an oily residue. The resulting hot residue was flushed with nitrogen then treated with toluene (221 kg) and the mass was stirred for at least 10 minutes at 40 to 50° C. The solution was employed as is in the subsequent step.

Example 4: Process for the Preparation of (S)-(−)-3-(4-Aminophenyl)-2-methoxypropionic acid (VI) and (S)-(−)-3-(4-Acetamidophenyl)-2-methoxypropionic acid (VII)

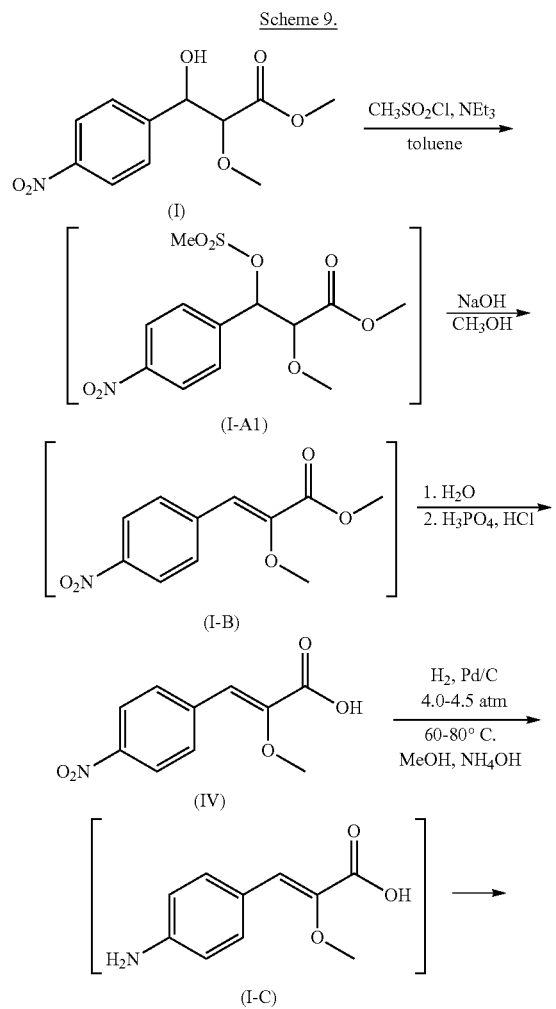

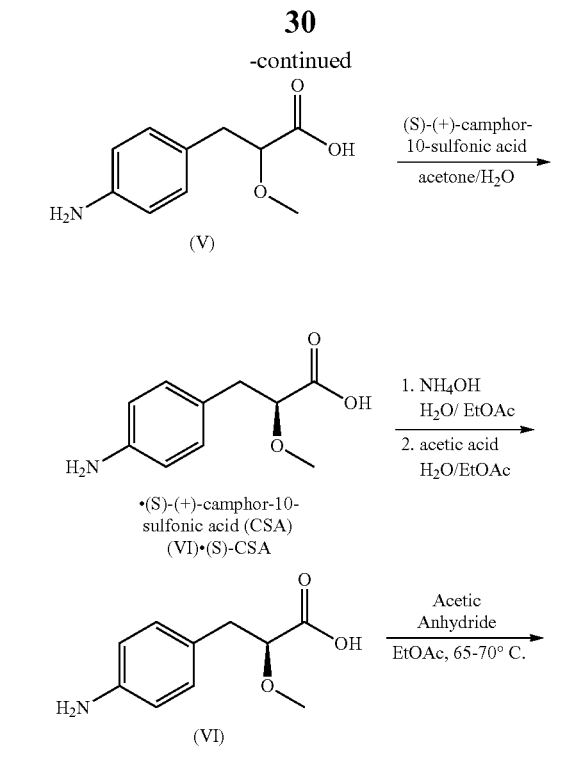

Preparation of 2-methoxy-3-(4-nitrophenyl)acrylic Acid (IV):

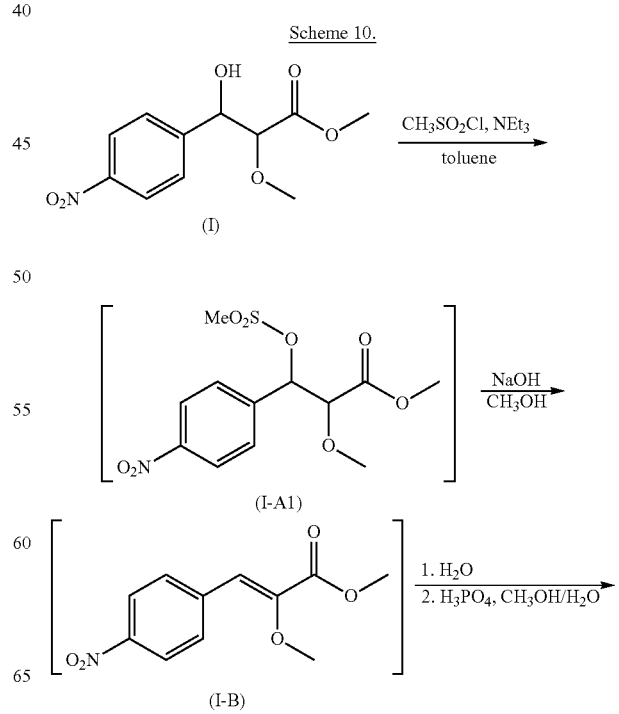

-continued

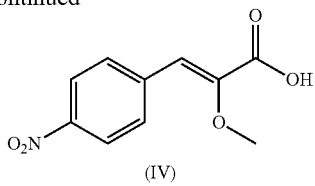

(IV)

TABLE 9

Batch formula at production scale (synthesis of compound (IV))

| Material | Factor* | Amount (kg) |
|---|---|---|
| methyl 3-hydroxy-2-methoxy-3-(4-nitrophenyl)propanoate, solution in toluene | 1.0 | All solution obtained in Scheme 8 |
| triethylamine | 0.9 | 42.8 |
| methanesulfonyl chloride | 0.8 | 38 |
| deionized water | 3.0 | 143 |
| Toluene | 0.15 | 7.1 |
| methanol | 3.1 | 147 |
| sodium hydroxide 30% | 1.86 | 88 |
| deionized water | 3.88 | 184 |
| hydrochloric acid 37% | 0.74 | 35.2 |
| phosphoric acid 85% | 0.16 | 7.6 |
| phosphoric acid 85% | — | to pH ≤3.0 |
| deionized water | 4.0 | 190 |
| toluene | 2.4 | 114 |

*factor is referenced to the amount of 4-nitrobenzaldehyde used

The methyl 3-hydroxy-2-methoxy-3-(4-nitrophenyl)propanoate (I) in toluene solution in a stainless steel reactor was cooled to 0 to 10° C. while flushing with nitrogen, and while maintaining the temperature at 0 to 10° C. triethylamine (42.8 kg) and methanesulfonyl chloride (38 kg) were added, and the reaction was stirred at 0 to 10° C. for 60 minutes. Deionized water (143 kg) was slowly added, and the resulting mass was stirred at 55 to 60° C. for 10 minutes, after which time stirring was stopped and the phases were allowed to separate. The aqueous phase was eliminated (199 kg) and the organic phase was filtered washing the filter with toluene (7.1 kg). The filtered solution was heated to 55 to 60° C. for 10 minutes. Stirring was stopped and the phases were allowed to separate; the possible aqueous phase was sent to the waste (3.5 kg). Under vacuum and under stirring an aliquot of the toluene was distilled taking into consideration the following proportion: for 50 kg of nitrobenzaldehyde used in Scheme 8, approximately 5 kg of toluene was distilled and this aliquot of distilled toluene was sent to waste. The toluene was removed by distillation under vacuum and without exceeding 60° C., to obtain an oily residue. The resulting residue was then treated with methanol (147 kg), flushed with nitrogen, cooled to 20 to 30° C. and treated slowly with 30% sodium hydroxide (88 kg). The reaction was stirred at 20 to 30° C. for 3 hours. Deionized water (184 kg) was added, and the solution heated to 60 to 65° C. At this temperature, 37% hydrochloric acid (35.2 kg) and 85% phosphoric acid (7.6 kg) were slowly added to precipitate the product. If necessary, 85% phosphoric acid was added to obtain pH≤3.0. The resulting precipitated product was stirred at 60 to 65° C. for at least 30 minutes then cooled to 35 to 40° C., and stirred for at least 30 minutes. The mixture was centrifuged washing with deionized water (190 kg) and then washed with toluene (114 kg), (mother liquor: 749 kg). The wet product (about 82 kg) was used in the next step.

Preparation of 3-(4-aminophenyl)-2-methoxypropanoic Acid (V):

Scheme 11.

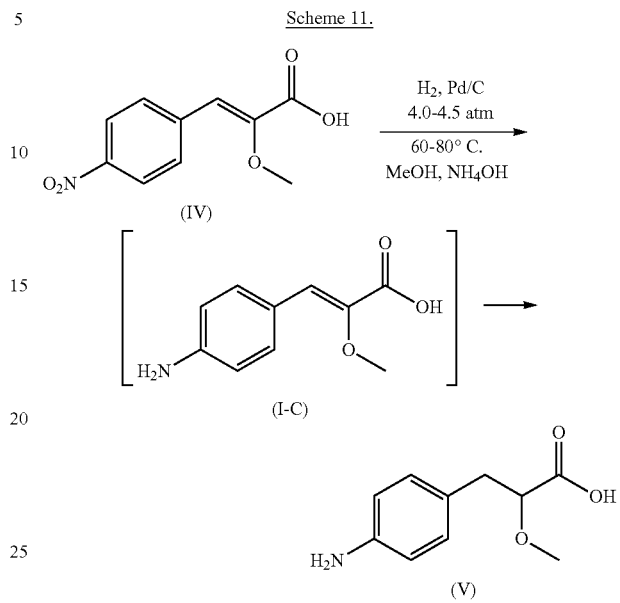

TABLE 10

Batch formula at production scale (synthesis of compound (V))

| Material | Factor* | Amount |
|---|---|---|
| 2-methoxy-3-(4- nitrophenyl)acrylic acid, wet | 1.0 | 82 |
| methanol | 3.0 | 143 |
| Ammonia 30% | 0.3 | 14.3 |
| deionized water | 0.2 | 9.5 |
| palladium on carbon 5% (containing 50% water) or palladium on carbon 5% (recycled) | 0.1 | 4.75 |
| deionized water | 0.05 | 2.4 |
| deionized water | 0.05 | 2.4 |
| deionized water | 0.05 | 2.4 |
| deionized water | 0.4 | 19 |
| deionized water | 2.0 | 95 |
| hydrochloric acid 37% | 0.32 | 15.2 |
| acetic acid 80% | 0.22 | 10.5 |
| ethyl acetate | 1.5 | 71 |
| deionized water | 1.0 | 47.5 |
| ethyl acetate | 1.0 | 47.5 |

*factor is referenced to the amount of 4-nitrobenzaldehyde used

Preparation of Aqueous Suspension of Palladium at 5% on Carbon in Water:

A suitable stainless steel reactor was loaded with deionized water (9.5 kg), 5% palladium on carbon (4.75 kg) and then the bag was washed twice with deionized water (2×2.4 kg).

Preparation of 3-(4-aminophenyl)-2-methoxypropanoic Acid (V):

A stainless steel reactor flushed with nitrogen (2×) was loaded with and wet 2-methoxy-3-(4-nitrophenyl)acrylic acid (IV) (82 kg), methanol (143 kg) and 30% ammonia (14.3 kg). After restoring the atmospheric pressure, the mixture was stirred at 20 to 30° C. up to complete dissolution. The resulting solution was flushed with nitrogen (2×) and treated with a previously prepared solution of 5% palladium on carbon in deionized water, and the empty vessel was washed with deionized water (2.4 kg). The reaction was flushed with nitrogen (2×), heated to 60 to 80° C. then charged with hydrogen until a pressure of 4.0 to 4.5 atm was obtained. The reaction was allowed to proceed, maintaining the pressure between 4.0 and 4.5 atm until hydrogen consumption ceased and the reaction was confirmed complete. The reactor was restored to atmospheric pressure and the reaction was cooled to 20 to 30° C., filtered through sparkler filter, flushed with nitrogen (2×) and treated with deionized water (19 kg) that was combined with the solution containing the product. Without exceeding 50° C., the solvent was distilled under stirring and under vacuum up to oily residue. The residue was treated with deionized water (95 kg), heated to 65 to 70° C. and the product precipitated by adding 37% hydrochloric acid (15.2 kg) and 80% acetic acid (10.5 kg). The mixture was stirred at 65 to 70° C. for at least 10 minutes, and then the mixture was treated with ethyl acetate (71 kg), flushed with nitrogen and stirred at 65 to 70° C. for at least 15 minutes. The reaction mass was cooled to 15 to 20° C. and stirred for at least 30 minutes. The suspension was centrifuged portion-wise washing with deionized water (47.5 kg) and ethyl acetate (47.5 kg). The moist product was dried at 60 to 70° C. to obtain 3-(4-aminophenyl)-2-methoxypropanoic acid (V) (40.5 kg).

Preparation of (S)-(−)-3-(4-Aminophenyl)-2-methoxypropionic acid S-(+)-camphor-10-sulfonic Acid Salt:

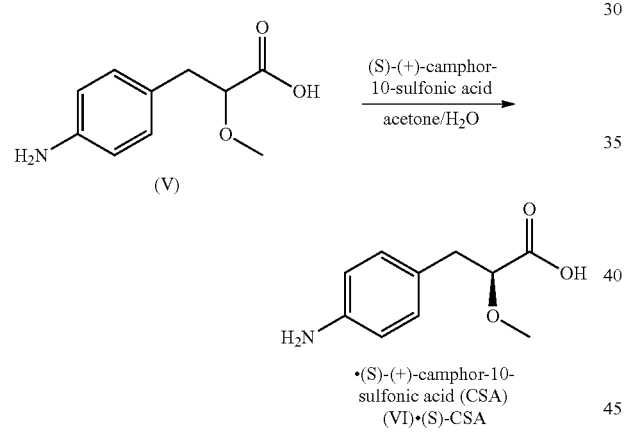

Scheme 12.

TABLE 11

Batch formula at production scale (synthesis of compound (VI)•(S)-CSA)

| Material | Factor* | Amount (kg) |
| --- | --- | --- |
| 3-(4-aminophenyl)-2-methoxypropanoic acid | 1.0 | 40.5 |
| (S)-(+)-10-camphor-sulfonic acid | 1.2321 | 49.9 |
| acetone | 2.0 | 81 |
| deionized water | 0.16 | 6.5 |
| acetone | 2.0 | 81 |
| acetone | 1.5 | 61 |

*factor is referenced to the amount of 3-(4-aminophenyl)-2-methoxypropanoic acid (dried) used A stainless steel reactor was loaded with 3-(4-aminophenyl)-2-methoxypropanoic acid (V) (40.5 kg) and (S)-(+)-camphor-10-sulfonic acid (49.9 kg); nitrogen was flushed and acetone (81 kg) was added. Deionized water (6.5 kg) was added. The reaction was heated to approximately 58° C. for 2 hours (reflux, dissolution does not occur). Acetone (81 kg) was added (temperature approximately 58° C.) and the reaction mass was kept at reflux (approx. 58° C.) for 1 hour. The reaction mass was then cooled to 37 to 42° C. and was centrifuged portion-wise washing with acetone (61 kg). The centrifuged product (S)-(−)-3-(4-aminophenyl)-2-methoxypropionic acid S-(+)-camphor-10-sulfonic acid salt (VI)•(S)-CSA (wet weight: 43.1 kg, 36.1 kg as dried) was used directly in the next step.

Preparation of (S)-(−)-3-(4-Aminophenyl)-2-methoxypropionic acid (VI):

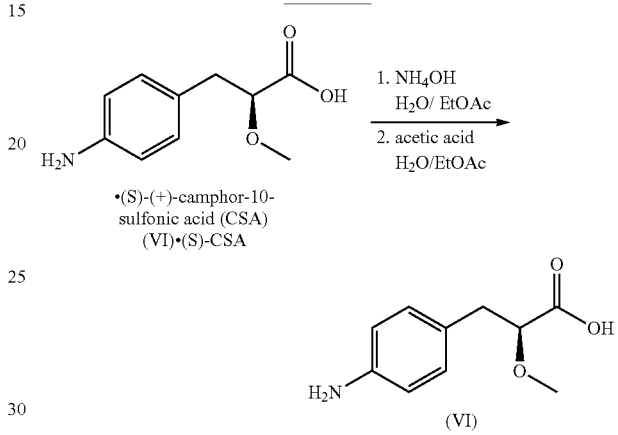

Scheme 13.

TABLE 12

Batch formula at production scale (synthesis of compound (VI))

| Material | Factor* | Amount (kg) |
| --- | --- | --- |
| deionized water | 2.0 | 72 |
| (S)-(−)-3-(4-Aminophenyl)-2-methoxypropionic acid S-(+)-camphor-10-sulfonic acid salt, wet | 1.0 | 43.1 (36.1 kg as dried) |
| deionized water | 0.2 | 7.2 |
| ethyl acetate | 1.0 | 36.1 |
| ammonia 30% | 0.1257 | 4.54 |
| acetic acid 80% | 0.05 | 1.81 |
| deionized water | 0.7 | 25.3 |
| ethyl acetate | 0.7 | 25.3 |

*factor is referenced to the amount of (S)-(−)-3-(4-aminophenyl)-2-methoxypropionic acid S-(+)-camphor-10-sulfonic acid salt used (as dried).

A stainless steel reactor was charged with deionized water (72 kg) and wet ((S)-(−)-3-(4-aminophenyl)-2-methoxypropionic acid S-(+)-camphor-10-sulfonic acid salt (VI)•(S)-CSA (wet weight: 43.1 kg, 36.1 kg as dried), flushed with nitrogen and heated for at least 10 minutes at 20 to 40° C. until complete dissolution occurred. The solution was filtered and washed with deionized water (7.2 kg), then ethyl acetate (36.1 kg). The resulting solution was flushed with nitrogen, heated to 55 to 60° C. and 30% ammonia (4.54 kg) was added to precipitate the product. The resulting mixture was stirred for at least 15 minutes at 55 to 60° C. then 80% acetic acid (1.81 kg) was added through a filter and the reaction flushed with nitrogen and stirred at 55 to 60° C. for at least 30 minutes then cooled down to 2-7° C. and stirred for at least 1 hour. The reaction mass was centrifuged portion-wise and washed with deionized water (25.3 kg), ethyl acetate (25.3 kg) to deliver wet (S)-(−)-3-(4-aminophenyl)-2-methoxypropionic acid (VI) (wet weight 11.8 kg, 10.8 kg as dried), which was used (wet) directly in the next step.

Preparation of (S)-(−)-3-(4-Acetamidophenyl)-2-methoxypropionic Acid (VII):

Scheme 14.

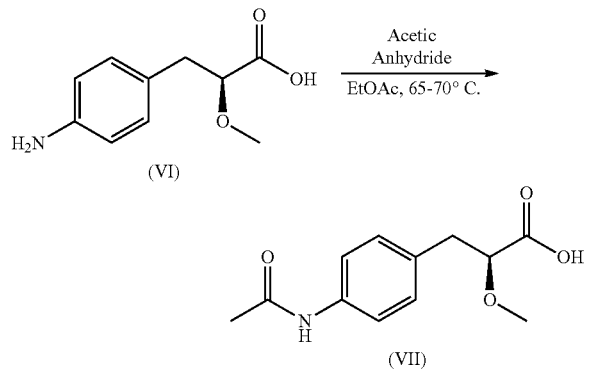

TABLE 13

Batch formula at production scale (synthesis of compound (VII))

| Material | Factor* | Amount (kg) |
| --- | --- | --- |
| Wet (S)-(−)-3-( 4-Aminophenyl)-2- methoxypropionic acid | 1.0 | 11.8 (10.8 kg as dried) |
| ethyl acetate | 1.5 | 16.2 |
| acetic anhydride | 0.65 | 7.0 |
| ethyl acetate | 0.5 | 5.4 |
| deionized water | 1.5 | 16.2 |

*factor is referenced to the amount of (S)-(−)-3-(4-aminophenyl)-2-methoxypropionic acid used (as dried)

A stainless steel reactor was charged with wet (S)-3-(4-aminophenyl)-2-methoxypropanoic acid (VI) (wet weight 11.8 kg, 10.8 kg as dried) and ethyl acetate (16.2 kg), under nitrogen. The mixture was heated to 65 to 70° C. and acetic anhydride (7.0 kg) was added through a cartridge filter over about 15 minutes. The reaction was stirred at 65 to 70° C. for 60 minutes and, once the reaction end was detected, continuously stirred until formation of a precipitate. The mixture was cooled to 10 to 20° C. and stirred at 10 to 20° C. for 30 minutes, then centrifuged and the resulting solid washed with ethyl acetate (5.4 kg), and deionized water (16.2 kg). The resulting product was dried at 60 to 70° C. for 13-16 hours, and milled to obtain (S)-3-(4-acetamidophenyl)-2-methoxypropanoic acid (VII) (12.3 kg).

Example 5: Preparation of methyl 3-hydroxy-2-methoxy-3-(4-nitrophenyl)propionate (I)

Scheme 15.

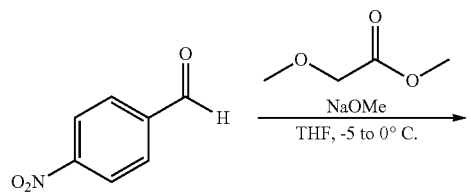

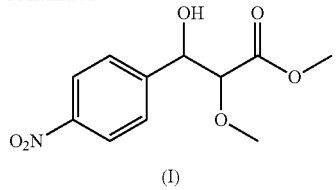

TABLE 14

Batch formula at production scale (synthesis of compound (I))

| Material | Factor* | Amount (kg) |
| --- | --- | --- |
| sodium methoxide | 0.6 | 228 |
| THF | 2.895 | 1100 |
| 4-nitrobenzaldehyde | 1.0 | 380 |
| methyl | 1.1 | 418 |
| THF | 1.0 | 380 |
| THF | 0.105 | 40 |
| cold toluene | 2.0 | 760 |
| glacial acetic acid | 0.75 | 285 |
| deionized water | 3.0 | 1140 |
| deionized water | 1.0 | 380 |
| sodium chloride | 0.1 | 38 |
| toluene | 1.0 | 380 |
| toluene | 4.65 | 1767 |

*factor is referenced to the amount of 4-nitrobenzaldehyde used

Preparation of 4-nitrobenzaldehyde in Methyl Methoxyacetate and Tetrahydrofuran Suspension:

A stainless steel reactor was charged with 4-nitrobenzaldehyde (380 kg), methyl methoxyacetate (418 kg) and tetrahydrofuran (380 kg) and cooled to −10 to −5° C. while stirring.

Preparation of Methyl 3-hydroxy-2-methoxy-3-(4-nitrophenyl)propionate (I):

A stainless steel reactor was flushed with nitrogen (2×), and charged with sodium methoxide (228 kg) and tetrahydrofuran (1100 kg) while flushing with nitrogen. The reactor was then flushed with nitrogen for 1 min and the sodium methoxide solution cooled to −15 to −10° C., while stirring. The cooled solution was then treated with the previously prepared suspension of 4-nitrobenzaldehyde in methyl methoxyacetate and tetrahydrofuran while maintaining the temperature of the reaction mass below 0° C. After the addition was complete, the empty reactor was rinsed with tetrahydrofuran (40 kg) and poured into the reaction. The reaction was stirred at −5 to 0° C. for no more than 5 minutes. Maintaining the temperature at −10 to 0° C., cold toluene (760 kg, −10 to 0° C.) and, at the same time, glacial acetic acid (285 kg) were quickly added and the reaction stirred for 10 minutes at −10 to +10° C. Deionized water (1140 kg) was added and the reaction mass stirred at 0 to 10° C. for at least 10 minutes, then at 25 to 30° C. for at least 10 minutes to ensure complete dissolution, after which time stirring was stopped and the phases were allowed to separate. The aqueous phase was eliminated, and the separated organic phase was treated with aqueous sodium chloride solution (previously prepared by adding 38 kg of sodium chloride to 380 kg of deionized water). The mass was then heated to 25 to 30° C., while stirring for at least 10 minutes. Stirring was stopped and the phases allowed to separate. The aqueous phase was eliminated. The separated organic phase was then distilled up to oily residue under vacuum, up to a temperature of 70 to 80° C. The reactor containing the hot residue was flushed with nitrogen then treated with toluene (380 kg), and the toluene distilled under vacuum, up to a temperature of 70 to 80° C., obtaining an oily residue. The resulting hot residue was flushed with nitrogen then treated with toluene (1767 kg) and the mass stirred for at least 10 minutes at 40 to 50° C. The solution was employed as is in the subsequent step.

Example 6: Process for the Preparation of (S)-(−)-3-(4-Aminophenyl)-2-methoxypropionic acid (VI) and (S)-(−)-3-(4-Acetamidophenyl)-2-methoxypropionic acid (VII)

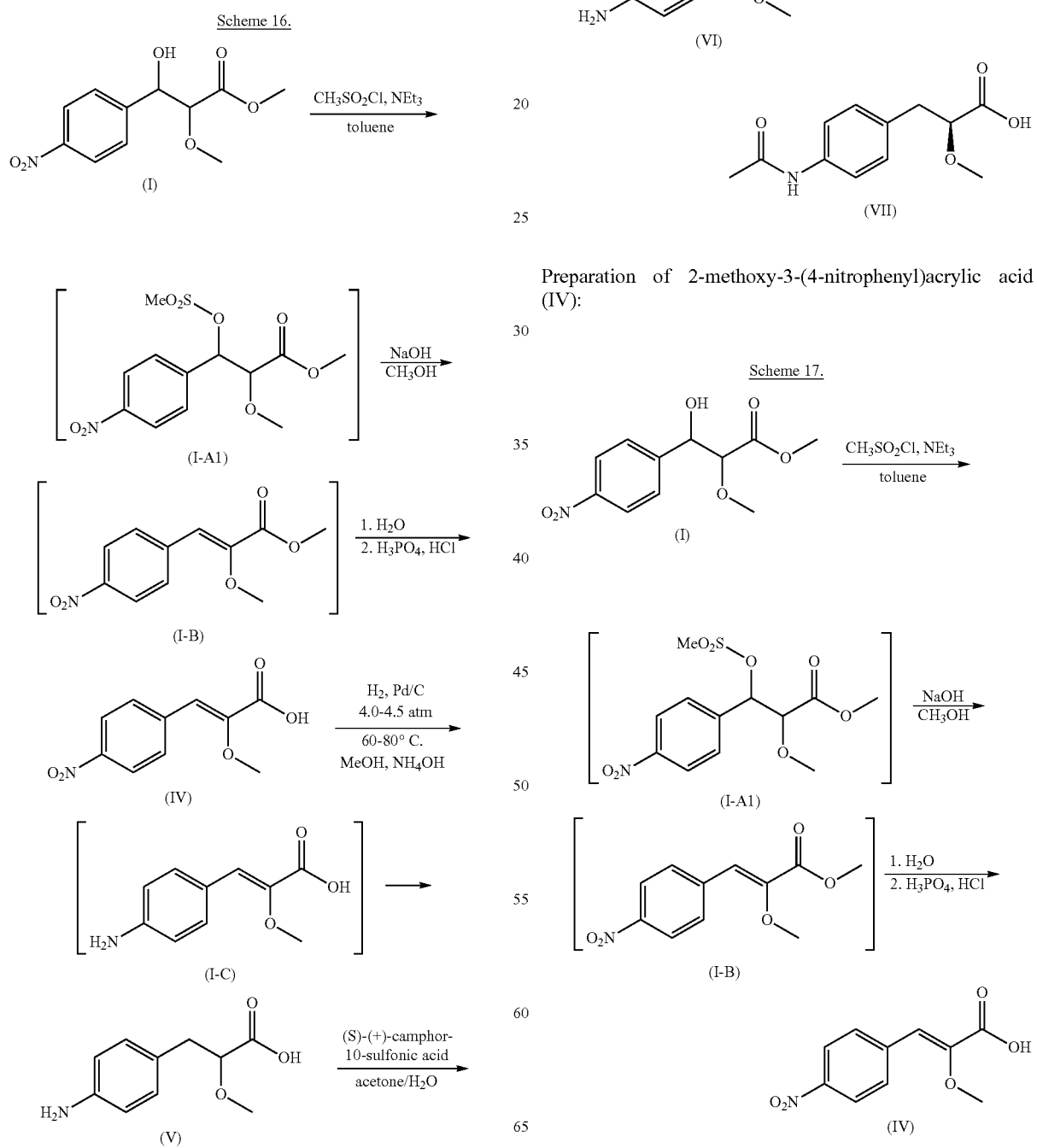

Preparation of 2-methoxy-3-(4-nitrophenyl)acrylic acid (IV):

TABLE 15

Batch formula at production scale (synthesis of compound (IV))

| Material | Factor* | Amount (kg) |
|---|---|---|
| methyl 3-hydroxy-2-methoxy-3-(4-nitrophenyl)propanoate, solution in toluene | 1.0 | All solution obtained in Scheme 15 |
| triethylamine | 0.9 | 342 |
| methanesulfonyl chloride | 0.8 | 304 |
| deionized water | 3.0 | 1140 |
| Toluene | 0.15 | 57 |
| methanol | 3.1 | 1178 |
| sodium hydroxide 30% | 1.86 | 707 |
| deionized water | 3.88 | 1474 |
| hydrochloric acid 37% | 0.74 | 281 |
| phosphoric acid 85% | 0.16 | 61 |
| phosphoric acid 85% | — | to pH ≤3.0 |
| deionized water | 4.0 | 1520 |
| toluene | 2.4 | 912 |

*factor is referenced to the amount of 4-nitrobenzaldehyde used

The methyl 3-hydroxy-2-methoxy-3-(4-nitrophenyl)propanoate (I) in toluene solution in a stainless steel reactor was cooled to 0 to 10° C. while flushing with nitrogen, and while maintaining the temperature at 0 to 10° C. triethylamine (342 kg) and methanesulfonyl chloride (304 kg) were added, and the reaction stirred at 0 to 10° C. for 60 minutes. Deionized water (1140 kg) was slowly added, and the resulting mass was stirred at 55 to 60° C. for 10 minutes, after which time stirring was stopped and the phases were allowed to separate. The aqueous phase was eliminated and the organic phase was filtered, washing the filter with toluene (57 kg). The filtered solution was heated to 55 to 60° C. for 10 minutes. Stirring was stopped and the phases were allowed to separate; the possible aqueous phase was sent to the waste. Under vacuum and under stirring distil an aliquot of the toluene taking into consideration the following proportion: for 380 kg of nitrobenzaldehyde used in Scheme 15, approximately 38 kg of toluene was distilled and this aliquot of distilled toluene was sent to waste. The toluene was removed by distillation under vacuum and without exceeding 60° C., to obtain an oily residue. The resulting residue was then treated with methanol (1178 kg), flushed with nitrogen, cooled to 20 to 30° C. and treated slowly with 30% sodium hydroxide (707 kg). The reaction was stirred at 20 to 30° C. for 3 hours. Deionized water (1474 kg) was added, and the solution heated to 60 to 65° C. At this temperature, 37% hydrochloric acid (281 kg) and 85% phosphoric acid (61 kg) were slowly added to precipitate the product. If necessary, 85% phosphoric acid was added to obtain pH≤3.0. The resulting precipitated product was stirred at 60 to 65° C. for at least 30 minutes then cooled to 35 to 40° C., and stirred for at least 30 minutes. The mixture was centrifuged washing with deionized water (1520 kg) and then washed with toluene (912 kg). The wet product (about 786 kg) was used in the next step.

Preparation of 3-(4-aminophenyl)-2-methoxypropanoic acid (V):

Scheme 18.

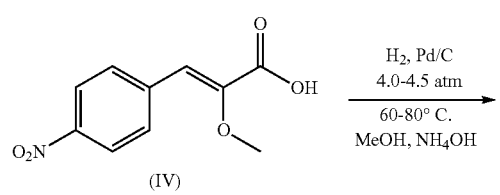

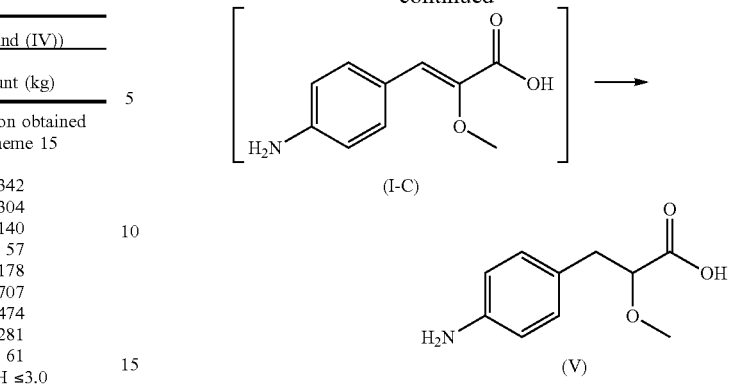

TABLE 16

Batch formula at production scale (synthesis of compound (V))

| Material | Factor* | Amount (kg) |
|---|---|---|
| 2-methoxy-3-(4-nitrophenyl)acrylic acid, wet | 1.0 | 786 |
| methanol | 3.0 | 1140 |
| Ammonia 30% | 0.3 | 114 |
| deionized water | 0.2 | 76 |
| palladium on carbon 5% (containing 50% water) or palladium on carbon 5% (recycled) | 0.1 | 38 |
| deionized water | 0.05 | 19 |
| deionized water | 0.05 | 19 |
| deionized water | 0.4 | 152 |
| deionized water | 2.0 | 760 |
| hydrochloric acid 37% | 0.32 | 122 |
| acetic acid 80% | 0.22 | 84 |
| ethyl acetate | 1.5 | 570 |
| deionized water | 1.0 | 380 |
| ethyl acetate | 1.0 | 380 |

*factor is referenced to the amount of 4-nitrobenzaldehyde used

Preparation of Aqueous Suspension of Palladium at 5% on Carbon in Water:

A suitable stainless steel reactor was loaded with deionized water (76 kg), 5% palladium on carbon (38 kg) and then the bag was washed with deionized water (19 kg).

Preparation of 3-(4-aminophenyl)-2-methoxypropanoic acid (V):

A stainless steel reactor flushed with nitrogen (2×) was loaded with wet 2-methoxy-3-(4-nitrophenyl)acrylic acid (IV) (786 kg), methanol (1140 kg) and 30% ammonia (114 kg). After restoring the atmospheric pressure, the mixture was stirred at 20 to 30° C. up to complete dissolution. The resulting solution was flushed with nitrogen (2×) and treated with a previously prepared solution of 5% palladium on carbon in deionized water, and the empty vessel was washed with deionized water (19 kg). The reaction was flushed with nitrogen (2×), heated to 60 to 80° C. then charged with hydrogen until a pressure of 4.0 to 4.5 atm was obtained. The reaction was allowed to proceed, maintaining the pressure between 4.0 and 4.5 atm until hydrogen consumption ceased and the reaction was confirmed complete. The reactor was restored to atmospheric pressure and the reaction was cooled to 20 to 30° C., filtered through sparkler filter, flushed with nitrogen (2×) and treated with deionized water (152 kg) that was combined with the solution containing the product. Without exceeding 50° C., the solvent was distilled under stirring and under vacuum up to oily residue. The residue was treated with deionized water (760 kg), heated to 65 to 70° C. and the product precipitated by adding 37% hydrochloric acid (122 kg) and 80% acetic acid (84 kg). The mixture was stirred at 65 to 70° C. for at least 10 minutes; at this stage it was confirmed that the pH was between 3.8 and 4.2 (not more than 4.2), and then the mixture was treated with ethyl acetate (570 kg), flushed with nitrogen and stirred at 65 to 70° C. for at least 15 minutes. The reaction mass was cooled to 15 to 20° C. and stirred for at least 30 minutes. The suspension was centrifuged portion-wise washing with deionized water (380 kg) and ethyl acetate (380 kg). The moist product was granulated, and dried at 60 to 70° C. to obtain 3-(4-aminophenyl)-2-methoxypropanoic acid (V) (~295 kg).

Preparation of (S)-(−)-3-(4-Aminophenyl)-2-methoxypropionic Acid S-(+)-camphor-10-sulfonic acid Salt:

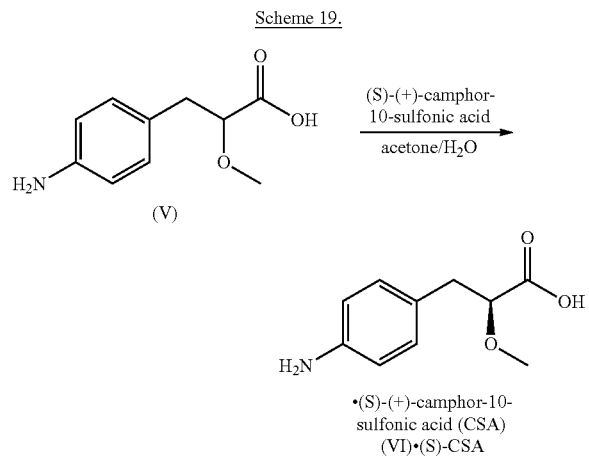

Scheme 19.

Starting material 3-(4-aminophenyl)-2-methoxypropanoic acid deriving from two batches were combined (one entire batch and an aliquot from a second one) to obtain the total amount of 400 kg of 3-(4-aminophenyl)-2-methoxypropanoic acid. This quantity is equivalent to the amount that would have been obtained starting from 500 kg of 4-nitrobenzaldehyde.

TABLE 17

Batch formula at production scale (synthesis of compound (VI)•(S)-CSA)

| Material | Factor* | Amount (kg) |
|---|---|---|
| 3-(4-aminophenyl)-2-methoxypropanoic acid | 1.0 | 400 |
| (S)-(+)-10-camphor-sulfonic | 1.2321 | 493 |
| acetone | 2.0 | 800 |
| deionized water | 0.16 | 64 |
| acetone | 2.0 | 800 |
| acetone | 1.5 | 600 |

*factor is referenced to the amount of 3-(4-aminophenyl)-2-methoxypropanoic acid (dried) used A stainless steel reactor was loaded with 3-(4-aminophenyl)-2-methoxypropanoic acid (V) (400 kg) and (S)-(+)-camphor-10-sulfonic acid (493 kg); nitrogen was flushed and acetone (800 kg) was added. Deionized water (64 kg) was added. The reaction was heated to approximately 58° C. for 1 hour (reflux, dissolution does not occur). Acetone (800 kg) was added (temperature approximately 58° C.) and the reaction mass was kept at reflux (approx. 58° C.) for 1 hour; the reaction mass was then cooled to 37 to 42° C. and was centrifuged portion-wise washing with acetone (600 kg) (between every centrifugation step, the suspension aliquot that was not involved in the centrifugation was first heated tan kept at 45 to 50° C. and then, before the subsequent centrifugation, the suspension was cooled again to 37 to 42° C.). The centrifuged product (S)-(−)-3-(4-aminophenyl)-2-methoxypropionic acid S-(+)-camphor-10-sulfonic acid salt (VI)•(S)-CSA (wet weight: 470 kg, 409.7 as dried) was used directly in the next step.

Preparation of (S)-(−)-3-(4-Aminophenyl)-2-methoxypropionic acid (VI):

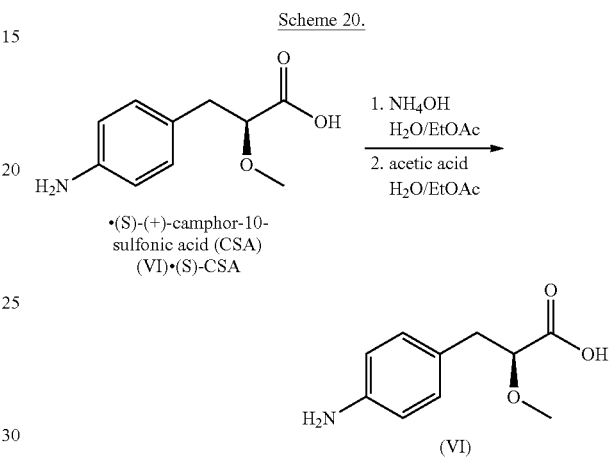

Scheme 20.

TABLE 18

Batch formula at production scale (synthesis of compound (VI))

| Material | Factor* | Amount (kg) |
|---|---|---|
| deionized water | 2.0 | 819 |
| (S)-(−)-3-(4-Aminophenyl)-2-methoxypropionic acid S-(+)-camphor-10-sulfonic acid salt, wet | 1.0 | 470 (409.7 kg as dried) |
| deionized water | 0.2 | 82 |
| ethyl acetate | 1.0 | 410 |
| ammonia 30% | 0.1257 | 51 |
| acetic acid 80% | 0.05 | 20.5 |
| deionized water | 0.7 | 287 |
| ethyl acetate | 0.7 | 287 |

*factor is referenced to the amount of (S)-(−)-3-(4-aminophenyl)-2-methoxypropionic acid S-(+)-camphor-10-sulfonic acid salt used (as dried).

A stainless steel reactor was charged with deionized water (819 kg) and wet ((S)-(−)-3-(4-aminophenyl)-2-methoxypropionic acid S-(+)-camphor-10-sulfonic acid salt (VI)•(S)-CSA (wet weight: 470 kg, 409.7 as dried), flushed with nitrogen and heated for at least 10 minutes at 20 to 40° C. until complete dissolution occurred. The solution was filtered washing with deionized water (82 kg), then ethyl acetate (410 kg). The resulting solution was flushed with nitrogen, heated to 55 to 60° C. and 30% ammonia (51 kg) was added to precipitate the product. The resulting mixture was stirred for at least 15 minutes at 55 to 60° C. then 80% acetic acid (20.5 kg) was added through a filter and the reaction flushed with nitrogen and stirred at 55 to 60° C. for at least 30 minutes then cooled down to 2-7° C. and stirred for at least 1 hour. The reaction mass was centrifuged portion-wise and washed with deionized water (287 kg), ethyl acetate (287 kg) to deliver wet (S)-(−)-3-(4-aminophenyl)-2-methoxypropionic acid (VI) (wet weight 162 kg, 138.8 kg as dried), which was used (wet) directly in the next step.

Preparation of (S)-(−)-3-(4-Acetamidophenyl)-2-methoxypropionic acid (VII):

Scheme 21.

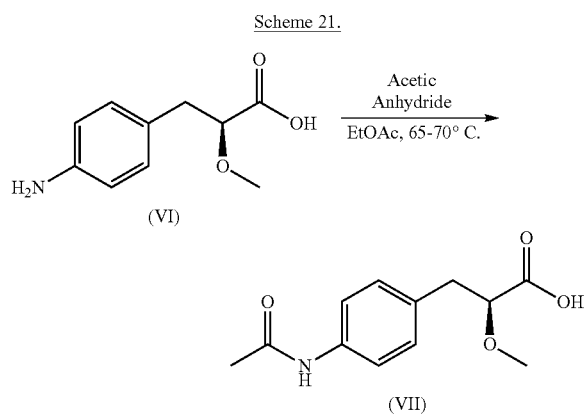

TABLE 19

Batch formula at production scale (synthesis of compound (VII))

| Material | Factor* | Amount (kg) |
| --- | --- | --- |
| Wet (S)-(−)-3-(4-Aminophenyl)-2-methoxypropionic acid | 1.0 | 162 (138.8 kg as dried) |
| ethyl acetate | 1.5 | 208 |
| acetic anhydride | 0.65 | 90 |
| ethyl acetate | 0.5 | 4.80 |
| deionized water | 1.5 | 208 |

*factor is referenced to the amount of (S)-(−)-3-(4-aminophenyl)-2-methoxypropionic acid used (as dried)

A stainless steel reactor was charged with wet (S)-3-(4-aminophenyl)-2-methoxypropanoic acid (VI) (wet weight 162 kg, 138.8 kg as dried) and ethyl acetate (208 kg), under nitrogen. The mixture was heated to 65 to 70° C. and acetic anhydride (90 kg) was added through a cartridge filter over about 15 minutes. The reaction was stirred at 65 to 70° C. for 90 minutes and, once the reaction end was detected, continuously stirred until formation of a precipitate. The mixture was cooled to 10 to 20° C. and stirred at 10 to 20° C. for 30 minutes, then centrifuged and the resulting solid washed with ethyl acetate (69 kg), and deionized water (208 kg). The resulting product was dried at 60 to 70° C. for 19 hours, and milled to obtain (S)-3-(4-acetamidophenyl)-2-methoxypropanoic acid (VII) (154.5 kg).

(S)-(−)-3-(4-Acetamidophenyl)-2-methoxypropionic acid (VII): IR: 3319, 2888, 2825, 1718, 1633, 1599, 1548, 1107 cm$^{-1}$; LCMS (+)ESI: m/z calculated for $C_{12}H_{15}N_4$: 237, found 236 (M−H)$^-$; $^1$H NMR (600 MHz, DMSO-d$_6$): δ 12.70 (s, 1H), 9.85 (s, 1H), 7.45 (d, 2H), 7.12 (d, 2H), 3.90 (dd, 1H), 3.20 (s, 3H), 2.80 (ABd, 2H), 2.00 (s, 3H). $^{13}$C NMR (600 MHz, DMSO-d$_6$): δ 24.09 (CH$_3$—CO—NH—), 37.94 (—C—CH$_2$—C—), 57.47 (CH$_3$—O—), 80.98 (—C—CH(O)—C—), 119.25 (2C, aromatic), 129.65 (2C, aromatic), 132.24 (1C, aromatic), 137.87 (1C, aromatic), 168.47 (CH$_3$—CO—NH—), 173.21 (—COOH). EA: C 60.82% (theor. 60.75%), H 6.44% (theor. 6.37%), N 5.91% (theor. 5.90%), O 26.97% (theor. 26.97%). DSC: melting 154-167° C. (onset 159° C.). Specific optical rotation: −22.7. (S)-3-(4-aminophenyl)-2-methoxypropanoic acid (HPLC): 0.06% (HPLC). Chiral purity (HPLC): 99.7% (HPLC). Residual solvents (ethyl acetate): 277 ppm (GC).

Example 7: X-Ray Crystal Structure Determination of Compound of Formula (VII)

The crystal used in the structural determination was obtained by vapour diffusion of a solution of compound of Formula (VII) and L-proline (2:1) in ethanol, using heptane as antisolvent. Single crystal X-ray diffraction analysis was performed. The results of this analysis are shown below. Refinement on the P2$_1$2$_1$2$_1$ space group lead to an R index of 0.062. The asymmetric unit is composed by two compound of Formula (VII) and two L-proline molecules.

Analysis of the single crystal diffraction data shows that the absolute configuration of the carbon alpha to the carboxylic acid group is (S). Based on these results, the absolute stereochemistry of the compound of Formula (VII) is shown in the structure below.

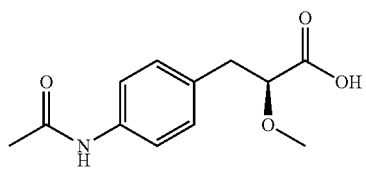 [SMILES: CO[C@@H](Cc1ccc(NC(C)=O)cc1)C(=O)O]

The optical rotation of the same compound, i.e., the compound of Formula (VII), is negative, which means is turns plane-polarized light to the left. The specification of the specific rotation for the pure compound is −26.0° to −19.0°. Accordingly, because the procedure for resolving the racemic mixture always employs the same reagents, characterization that the product obtained has the (S) configuration is confirmed by specific optical rotation.

In addition, the chiral purity (HPLC) of the compound of Formula (VII) can be determined, for example using the method described herein.

The crystal data and structure refinement for the single crystal X-ray diffraction of the compound of Formula (VII): L-proline derivative is set out below.

| | |
| --- | --- |
| Empirical formula | $C_{17}H_{24}N_2O_6$ |
| Formula weight | 352.38 |
| Temperature | 296(2) K |
| Diffractometer | Bruker Smart-Apex (area detector) |
| Wavelength | 0.71073 Å |
| Crystal system | Orthorhombic |
| Space group | P2$_1$2$_1$2$_1$ |
| Unit cell dimensions | a = 7.7813(5) Å   α = 90° |
| | b = 9.5414(6) Å   β = 90° |
| | c = 49.006(3) Å   γ = 90° |
| Volume | 3638.4(4) Å$^3$ |
| Z | 8 |
| Density (calculated) | 1.287 Mg/m$^3$ |
| Absorption coefficient | 0.098 mm$^{-1}$ |
| F(000) | 1504 |
| Crystal size | 0.49 × 0.25 × 0.08 mm$^3$ |
| Theta range for data collection | 0.83 to 28.75°. |
| Index ranges | −10 <= h <= 8, −12 <= k <= 12, −54 <= l <= 63 |
| Reflections collected | 19513 |
| Independent reflections | 8598 [R(int) = 0.0437] |
| Completeness to theta = 25.00° | 99.7% |
| Absorption correction | Semi-empirical from equivalents |
| Max. and min transmission | 0.992 and 0.777 |
| Refinement method | Full-matrix least-squares on F$^2$ |
| Data/restraints/parameters | 8598/0/474 |
| Goodness-of-fit on F$^2$ | 0.984 |

-continued

| | |
|---|---|
| Final R indices [I > 2sigma(I)] | R1 = 0.0623, wR2 = 0.1517 |
| R indices (all data) | R1 = 0.1217, wR2 = 0.1843 |
| Absolute structure parameter | −0.8(13) |
| Largest diff. peak and hole | 0.382 and −0307 e · Å$^{-3}$ |
| Computing programs (Bruker) | Smart 5.6/Saint 5.0/Shelxtl-NT 6.1 |

INCORPORATION BY REFERENCE

All publications and patents mentioned herein, including those items listed below, are hereby incorporated by reference in their entirety for all purposes as if each individual publication or patent was specifically and individually incorporated by reference. In case of conflict, the present application, including any definitions herein, will control.

EQUIVALENTS

While specific embodiments of the subject disclosure have been discussed, the above specification is illustrative and not restrictive. Many variations of the disclosure will become apparent to those skilled in the art upon review of this specification. The full scope of the disclosure should be determined by reference to the claims, along with their full scope of equivalents, and the specification, along with such variations.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present disclosure.

What is claimed is:

1. A process for preparing a substantially optically pure compound of Formula (VII):

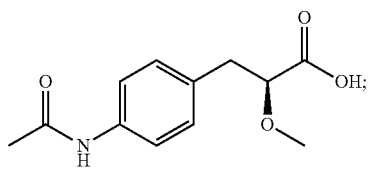
(VII)

the process comprising:
reacting a compound of Formula (I):

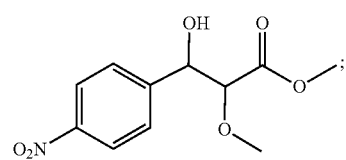
(I)

with an activating agent, in the optional presence of a base, to form an intermediate of Formula (I-A):

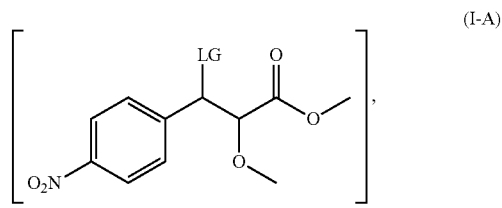
(I-A)

wherein LG is a leaving group;
treating the intermediate of Formula (I-A) with a base solution in the presence of an alcohol solvent, to eliminate the leaving group and thereby forming an intermediate of Formula (I-B):

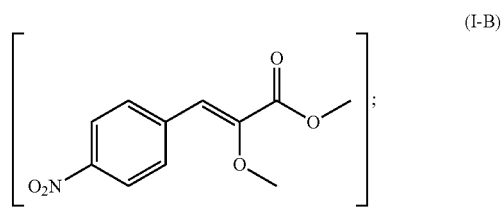
(I-B)

hydrolyzing the intermediate of Formula (I-B) to form a compound of Formula (IV):

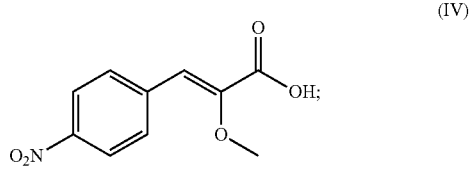 [SMILES: CO/C(=C\c1ccc([N+](=O)[O-])cc1)C(=O)O]
(IV)

hydrogenating the compound of Formula (IV) to form a compound of Formula (V):

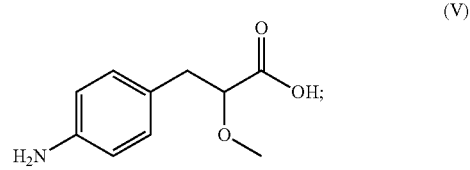
(V)

resolving the compound of Formula (V) to form a substantially optically pure compound of Formula (VI):

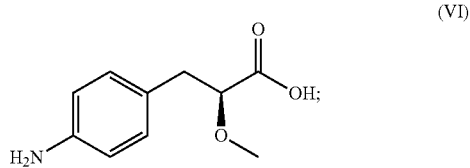
(VI)

and
  acylating the compound of Formula (VI) to form the compound of Formula (VII).

2. The process of claim 1, wherein reacting a compound of Formula (I) with an activating agent comprises reacting in the presence of the base and a solvent.

3. The process of claim 2, wherein the solvent in the reacting step is selected from the group consisting of toluene, dichloromethane, tetrahydrofuran, diethyl ether, 2-methyltetrahydrofuran, and acetonitrile.

4. The process of claim 1, wherein the base in the reacting step is an amine base.

5. The process of claim 1, wherein the activating agent is methanesulfonyl chloride.

6. The process of claim 1, wherein the leaving group is —OSO$_2$Me.

7. The process of claim 1, wherein the alcohol solvent comprises methanol.

8. The process of claim 1, wherein the base solution comprises sodium hydroxide.

9. The process of claim 1, wherein hydrolyzing the intermediate of Formula (I-B) to form a compound of Formula (IV) comprises:
  (i) contacting the intermediate of Formula (I-B) with an alkali hydroxide and water; and
  neutralizing to form the compound of Formula (IV).

10. The process of claim 9, wherein neutralizing comprises acidifying to a pH of less than or equal to 3 with an acid.

11. The process of claim 1, wherein hydrogenating the compound of Formula (IV) to form a compound of Formula (V) comprises contacting the compound of Formula (IV) with hydrogen and a catalyst.

12. The process of claim 1, wherein resolving the compound of Formula (V) to form a substantially optically pure compound of Formula (VI) comprises:
  (a) resolving a compound of Formula (V) in the presence of a chiral acid thereby forming a chiral salt of the compound of Formula (VI); and
  (b) neutralizing the chiral salt of the compound of Formula (VI) thereby forming the compound of Formula (VI).

13. The process of claim 12, wherein the chiral salt of the compound of Formula (VI) is:

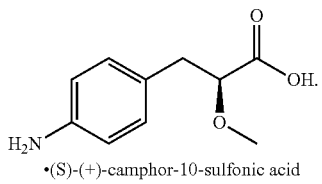

•(S)-(+)-camphor-10-sulfonic acid

14. The process of claim 12, wherein neutralizing comprises contacting the chiral salt of the compound of Formula (VI), with (i) an aqueous base; and then (ii) acidifying the solution by adding an acid.

15. The process of claim 1, wherein acylating comprises contacting the compound of Formula (VI) with acetic anhydride in the presence of an organic solvent selected from the group consisting of ethyl acetate, tetrahydrofuran, diethyl ether, dichloromethane, and toluene.

16. The process of claim 1, wherein the substantially optically pure compound of Formula (VII) is at least 98% of the enantiomer:

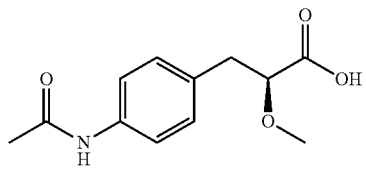

expressed as a percentage of both enantiomers.

17. A process for preparing a compound of Formula (I):

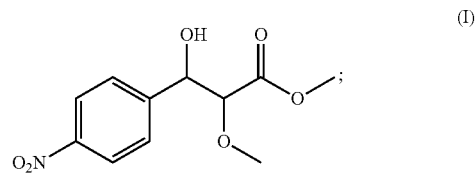 [SMILES: COC(=O)C(OC)C(O)c1ccc([N+](=O)[O-])cc1]

the process comprising, providing a mixture of a compound of Formula (II):

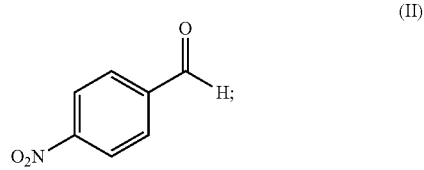

and a compound of Formula (III):

and contacting the mixture with a base; thereby forming a compound of Formula (I).

18. The process of claim 17, wherein contacting occurs in tetrahydrofuran.

19. A compound represented by:

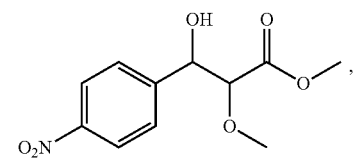 [SMILES: COC(=O)C(OC)C(O)c1ccc([N+](=O)[O-])cc1]

or a pharmaceutically acceptable salt thereof.

* * * * *